(12) United States Patent
Gungor et al.

(10) Patent No.: US 7,205,322 B2
(45) Date of Patent: Apr. 17, 2007

(54) THIAZOLIDINE COMPOUNDS AS CALCIUM SENSING RECEPTOR MODULATORS

(75) Inventors: Timur Gungor, Pennington, NJ (US); John K. Dickson, Jr., Apex, NC (US)

(73) Assignee: Bristol-Myers Squibb Company, Princeton, NJ (US)

( * ) Notice: Subject to any disclaimer, the term of this patent is extended or adjusted under 35 U.S.C. 154(b) by 145 days.

(21) Appl. No.: 10/775,742

(22) Filed: Feb. 10, 2004

(65) Prior Publication Data

US 2004/0242602 A1 Dec. 2, 2004

Related U.S. Application Data

(60) Provisional application No. 60/446,859, filed on Feb. 12, 2003.

(51) Int. Cl.
| | |
|---|---|
| A61K 31/426 | (2006.01) |
| A61K 31/427 | (2006.01) |
| C07D 277/04 | (2006.01) |
| C07D 417/06 | (2006.01) |
| C07D 417/12 | (2006.01) |

(52) U.S. Cl. ..................... 514/365; 548/146
(58) Field of Classification Search ............... 548/146; 514/365
See application file for complete search history.

(56) References Cited

U.S. PATENT DOCUMENTS

| | | | |
|---|---|---|---|
| 4,411,890 | A | 10/1983 | Momany |
| 5,688,938 | A | 11/1997 | Brown et al. |
| 5,763,569 | A | 6/1998 | Brown et al. |
| 6,022,894 | A | 2/2000 | Del Mar et al. |
| 6,031,003 | A | 2/2000 | Nemeth et al. |
| 6,211,244 | B1 | 4/2001 | Van Wagenen et al. |
| 6,673,821 | B2 * | 1/2004 | Wang et al. ............... 514/365 |

FOREIGN PATENT DOCUMENTS

| | | |
|---|---|---|
| EP | 0342613 B1 | 11/1992 |
| EP | 0449011 B1 | 10/1997 |
| WO | WO 89/07110 | 8/1989 |
| WO | WO 89/07111 | 8/1989 |
| WO | WO 93/04081 | 3/1993 |
| WO | WO 94/18959 | 9/1994 |
| WO | WO 97/37967 | 10/1997 |
| WO | WO 98/45255 | 10/1998 |
| WO | WO 99/51241 | 10/1999 |
| WO | WO 99/51569 | 10/1999 |
| WO | WO 00/45816 | 8/2000 |
| WO | WO 01/08673 A1 | 2/2001 |

OTHER PUBLICATIONS

Arndt, D., "Mangan-Verbindungen als Oxidationsmittel in der organischen Chemie", Methoden der Organischen Chemie (Houben-Weyl), Fourth Edition, vol. 4, Part 1b, Georg Thieme Verlag, Stuttgart, publ., Müller, E., ed., pp. 466-672 (1975).

Betts, M.J. et al., "'Hidden' axial chirality as a stereodirecting element in reactions involving enol(ate) intermediates. Part 2. Cyclisation reactions of methyl (4R)-3-(2-diazo-3-oxobutanoyl)-1, 1-dioxo-1λ⁶, 3-(and 1-oxo-1λ⁴, 3-) thiazolidine-4-carboxylates", J. Chem. Soc., Perkin Trans. 1, pp. 1067-1072 (1999).

Bundgaard, H., Chapter 5: "Design and Application of Prodrugs", A Textbook of Drug Design and Development, Harwood Academic Publishers, publ., Krogsgaard-Larsen, P. et al., eds., pp. 113-191 (1991).

Bundgaard, H., ed., Design of Prodrugs, Elsevier Science Publishers B.V., publ. (1985) (table of contents).

Cagniant, P. et al., "No. 50. Sur la synthése de quelques amines arylaliphatiques dérivées du β-méthyl-naphtaléne", Bull. Soc. Chim. Fr., pp. 349-353 (1943).

Edwards, J.P. et al., "Nonsteroidal Androgen Receptor Agonists Based on 4-(trifluoromethyl)-2H-pyrano[3,2-g]quinolin-2-one", Bioorganic & Medicinal Chemistry Letters, vol. 9, pp. 1003-1008 (1999).

Florvall, L. et al., "Selective Monoamine Oxidase Inhibitors. 3. Cyclic Compounds Related to 4-Aminophenethylamine. Preparation and Neuron-Selective Action of Some 5-(2-Aminoethyl)-2,3-dihydroindoles", J. Med. Chem., vol. 29, No. 8, pp. 1406-1412 (1986).

Gowen, M. et al., "Antagonizing the parathyroid calcium receptor stimulates parathyroid hormone secretion and bone formation in osteopenic rats", The Journal of Clinical Investigation, vol. 105, No. 11, pp. 1595-1604 (2000).

Greene, T.W. et al., Protecting Groups in Organic Synthesis, Third Edition, John Wiley & Sons, Inc., publ. (1999) (table of contents).

Greenstein, J.P. et al., Chemistry of the Amino Acids, vol. 3, Robert E. Krieger Publishing Company, Inc., publ., pp. v-xiii (table of contents) (1984).

Hamann, L.G. et al., "Discovery of a Potent, Orally Active, Nonsteroidal Androgen Receptor Agonist: 4-Ethyl-1,2,3,4-tetrahydro-6-(trifluoromethyl)-8-pyridono[5,6-g]-quinoline (LG121071)", J. Med. Chem., vol. 42, pp. 210-212 (1999).

Lee, D.G., Chapter 11: "Phase Transfer Assisted Permanganate Oxidations", Oxidation in Organic Chemistry, Part D, Academic Press, publ., Trahanovsky, W.S., ed., pp. 147-204 (1982).

(Continued)

Primary Examiner—Laura L. Stockton
(74) Attorney, Agent, or Firm—Burton Rodney

(57) ABSTRACT

The present invention relates to modulators of the calcium sensing receptor having the formula I

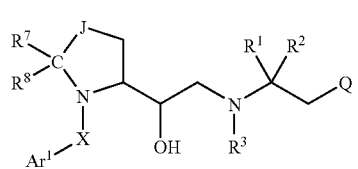

wherein
$Ar^1$, X, J, $R^1$, $R^2$, $R^3$, $R^7$, $R^8$ and Q are as defined herein.

8 Claims, No Drawings

OTHER PUBLICATIONS

Moed, H.D. et al., "Synthesis of β-phenyl-ethylamine Derivaties. III) Bronchodilators", Recl. Trav. Chim. Pays-Bas, vol. 74, pp. 919-936 (1955).

Neer, R.M. et al., "Effect of Parathyroid Hormone (1-34) on Fractures and Bone Mineral Density in Postmenopausal Women with Osteoporosis", The New England Journal of Medicine, vol. 344, No. 19, pp. 1434-1441 (2001).

Nichols, D.E. et al., "Effects of Certain Hallucinogenic Amphetamine Analogues on the Release of [$^3$H]Serotonin from Rat Brain Synaptosomes", J. Med. Chem., vol. 25, No. 5, pp. 530-535 (1982).

Norris, R.K. et al., "Kinetics and Stereochemistry of Elimination of Nitrous Acid from 1-$p$-Nitrophenyl-2-nitroethyl Derivatives", Aust. J. Chem., vol. 39, pp. 281-294 (1986).

Stewart, R., Chapter 1: "Oxidation by Permanganate", Oxidation in Organic Chemistry, Part A, Academic Press, publ., Wiberg, K.B., ed., pp. 1-68 (1965).

Wermuth, C.G. et al., Chapter 31: "Designing Prodrugs and Bioprecursors I: Carrier Prodrugs", The Practice of Medicinal Chemistry, Academic Press, publ., Wermuth, C.G., ed., pp. 671-696 (1996).

Whitfield, J.F. et al., "Parathyroid Hormone, Its Fragments and Their Analogs for the Treatment of Osteoporosis", Treat. Endocrinol., vol. 1, No. 3, pp. 175-190 (2002).

Brown, E.M. et al., "Cloning and characterization of an extracellular $Ca^{2+}$-sensing receptor from bovine parathyroid", Nature, vol. 366, pp. 575-580 (1993).

Hudlicky, M., Oxidations in Organic Chemistry: ACS Monograph 186, American Chemical Society, publ., pp. ix-xiii (table of contents) (1990).

Larock, R.C., Comprehensive Organic Transformations: A Guide to Functional Group Preparations, VCH Publishers, Inc., publ., pp. xiii-xxviii (table of contents) (1989).

Zaragoza, F. et al., "(Cyanomethyl)trialkylphosphonium Iodides: Efficient Reagents for the Intermolecular Alkylation of Amines with Alcohols in Solution and on Solid Phase", J. Org. Chem., vol. 66, No. 7, pp. 2518-2521 (2001).

\* cited by examiner

THIAZOLIDINE COMPOUNDS AS CALCIUM SENSING RECEPTOR MODULATORS

CROSS-REFERENCE TO RELATED APPLICATION

This application claims the benefit of U.S. Provisional Application No. 60/446,859 filed Feb. 12, 2003 which is incorporated herein by reference in its entirety.

FIELD OF THE INVENTION

The present invention relates to novel thiazolidine compounds, pharmaceutical compositions containing these compounds and their use as modulators of the calcium sensing receptor.

BACKGROUND OF THE INVENTION

Certain cells in the body respond not only to chemical signals, but also to ions such as extracellular calcium ions ($Ca^{2+}$). Changes in the concentration of extracellular $Ca^{2+}$ (referred to herein as "$[Ca^{2+}]$") alter the functional responses of these cells. One such specialized cell is the parathyroid cell which secretes parathyroid hormone (PTH). PTH is the principal endocrine factor regulating $Ca^{2+}$ homeostasis in the blood and extracellular fluids.

PTH, by acting on bone and kidney cells, increases the level of $Ca^{2+}$ in the blood. This increase in $[Ca^{2+}]$ then acts as a negative feedback signal, depressing PTH secretion. The reciprocal relationship between $[Ca^{2+}]$ and PTH secretion forms the essential mechanism maintaining bodily $Ca^{2+}$ homeostasis.

Extracellular $Ca^{2+}$ acts directly on parathyroid cells to regulate PTH secretion. The existence of a parathyroid cell surface protein which detects changes in $[Ca^{2+}]$ has been confirmed (see Brown et al., Nature 366:574, 1993). In parathyroid cells, this protein, the calcium sensing receptor, acts as a receptor for extracellular $Ca^{2+}$, detects changes in the ion concentration of extracellular $Ca^{2+}$, and initiates a functional cellular response, PTH secretion.

Extracellular $Ca^{2+}$ influences various cell functions, as reviewed in Nemeth et al., Cell Calcium 11:319, 190. Specifically, the osteoclast in bone, the juxtaglomerular, proximal tubule cells in the kidney, the keratinocyte in the epidermis, the parafollicular cell in the thyroid, intestinal cells, and the trophoblast in the placenta, have the capacity to sense changes in $[Ca^{2+}]$. It has been suggested that cell surface calcium sensing receptors may also be present on these cells, imparting to them the ability to detect and to initiate or enable a response to changes in $[Ca^{2+}]$.

Accordingly, compounds which mimic the effects of extracellular $Ca^{2+}$ on a calcium sensing receptor molecule may be useful as calcium modulators which are active at $Ca^{2+}$ receptors. Such compounds could be useful in the treatment of various disease states characterized by abnormal levels of one or more components, e.g., polypeptides, such as hormones, enzymes or growth factors, the expression and/or secretion of which is regulated or affected by activity at one or more $Ca^{2+}$ receptors. Target diseases or disorders for these compounds include diseases involving abnormal bone and mineral homeostasis.

Abnormal calcium homeostasis may be characterized by one or more of the following activities: abnormal increase or decrease in serum calcium; an abnormal increase or decrease in urinary excretion of calcium; an abnormal increase or decrease in bone calcium levels (for example, as assessed by bone mineral density measurements); an abnormal absorption of dietary calcium; an abnormal increase or decrease in the production and/or release of messengers which affect serum calcium levels, such as PTH and calcitonin; and an abnormal change in the response elicited by messengers which affect serum calcium levels.

In extensive animal experiments and in clinical trials, intermittent injection of low doses of PTH has been shown to be a safe and effective stimulator of bone formation (see Whitfiled J F, et al. (2002) Treat Endocrinol (2002) 1(3): 175–190). A double blind, randomized, placebo-controlled trial in postmenopausal women, the PTH peptide fragment (1–34) was shown to reduce the risk of spine fractures and non-traumatic, non-spine fractures 65% and 54%, respectively (Neer R M, et al. (2001) N Engl J Med 344:1434–1441). In contrast to the anabolic effects observed after intermittent administration, it is well documented that continuous exposure to the hormone results in increases in bone turnover with a subsequent loss in bone mass.

Other than applying a PTH peptide fragment, conceivably, one could make use of the endogenous stores of PTH in the parathyroid gland, in order to stimulate bone formation through the release of PTH.

Proof-of-principle for the calcilytic approach includes a study in osteopenic ovariectomized (OVX) rats in which oral administration of a calcilytic agent NPS-2143 (Gowen M, et al. (2000) J. Clin. Invest. 105:1595–1604) resulted in an increase in bone mass in the presence of an antiresorptive agent. Intravenous bolus injection of NPS-2143 resulted in a transient increase in serum PTH compatible with the anabolic profile of the hormone. These results indicate that calcilytic agents can serve as a novel class of anabolic agents for the treatment of established osteoporosis.

Thus, the identification of compounds which demonstrate activity as calcium sensing receptor modulators, preferably calcium sensing receptor antagonists, would be of significant value for the treatment of diseases or disorders associated with abnormal bone or mineral homeostasis.

SUMMARY OF THE INVENTION

In accordance with the present invention, compounds are provided which are capable of modulating the function of a calcium sensing receptor, preferably the compounds are antagonists of the calcium sensing receptor, and have the general formula I

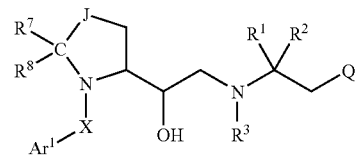

I wherein $Ar^1$ is a substituted or unsubstituted aryl or substituted or unsubstituted heteroaryl;

X is a linking group selected from alkylene, CO, alkyleneCO, OCO, alkyleneOCO, $SO_2$ and alkylene$SO_2$;

J is a linking group selected from S, SO and $SO_2$;

$R^1$ and $R^2$ are each independently substituted or unsubstituted $C_1$–$C_4$ alkyl, or $R^1$ can be cyclized with $R^2$ to form (—$CH_2$—)$_m$ where m is an integer from 2 to 5;

$R^3$ is hydrogen (H) or alkyl;

Q is $Ar^1$ or G;

G is

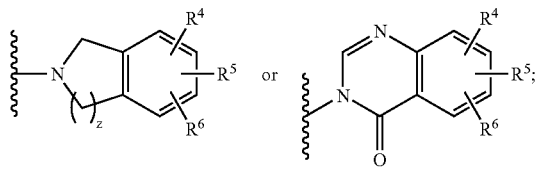

z is 1 or 2;

$R^4$, $R^5$ and $R^6$ are each independently selected from hydrogen (H), halo, haloalkyl, alkyl, alkoxy, haloalkoxy, hydroxy, cyano, nitro, amino, alkylamino and alkylthio;

$R^7$ and $R^8$ are each independently selected from hydrogen (H), alkyl, aryl and heteroaryl.

The definition of formula I above includes all pharmaceutically acceptable salts, stereoisomers and prodrug esters of formula I.

The compounds of formula I function as modulators of the calcium sensing receptor. Preferably, the compounds of formula I exhibit activity as antagonists of the calcium sensing receptor and may be used in the treatment of diseases or disorders associated with calcium sensing receptor activity, such as abnormal bone and mineral homeostasis, particularly, hypoparathyroidism, osteosarcoma, chondrosarcoma, periodontal disease, fracture healing, osteoarthritis, Paget's disease, osteopenia, glucocorticoid-induced osteomalacia, osteoporosis, metastatic bone disease or joint replacement.

The present invention provides for compounds of formula I, pharmaceutical compositions employing such compounds and for methods of using such compounds. In particular, the present invention provides for a pharmaceutical composition comprising a therapeutically effective amount of a compound of formula I, alone or in combination with a pharmaceutically acceptable carrier.

Further, in accordance with the present invention, a method is provided for preventing, inhibiting or treating the progression or onset of diseases or disorders associated with calcium sensing receptor activity, such as the diseases or disorders defined above and hereinafter, wherein a therapeutically effective amount of a compound of formula I is administered to a mammalian, i.e., human, patient in need of treatment.

The compounds of the invention can be used alone, in combination with other compounds of the present invention, or in combination with one or more other agent(s) active in the therapeutic areas described herein.

In addition, a method is provided for preventing, inhibiting or treating the diseases as defined above and hereinafter, wherein a therapeutically effective amount of a combination of a compound of formula I and another type of therapeutic agent, is administered, concurrently or sequentially, to a human patient in need of treatment.

Further preferred embodiments include compounds of formula I wherein:

X is alkylene;

J is sulfur (S);

$R^1$ and $R^2$ are methyl, or $R^1$ is cyclized with $R^2$ to form a cyclopropyl ring;

$R^3$ is hydrogen;

z is 2;

Q is substituted or unsubstituted phenyl or naphthyl, or G;

$R^4$, $R^5$ and $R^6$ are hydrogen; and $R^7$ and $R^8$ are hydrogen.

DETAILED DESCRIPTION OF THE INVENTION

[1] Thus, in a first embodiment, the present invention provides for a compound of formula I

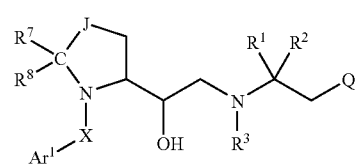

I wherein:

$Ar^1$ is a substituted or unsubstituted aryl or substituted or unsubstituted heteroaryl;

X is a linking group selected from alkylene, CO, alkyleneCO, OCO, alkyleneOCO, $SO_2$ and alkylene$SO_2$;

J is a linking group selected from S, SO and $SO_2$;

$R^1$ and $R^2$ are each independently substituted or unsubstituted $C_1$–$C_4$ alkyl, or $R^1$ can be cyclized with $R^2$ to form $(-CH_2-)_m$ where m is an integer from 2 to 5;

$R^3$ is hydrogen (H) or alkyl;

Q is $Ar^1$ or G;

G is

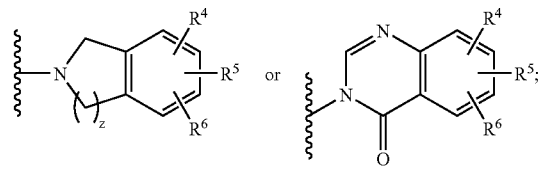

z is 1 or 2;

$R^4$, $R^5$ and $R^6$ are each independently selected from hydrogen (H), halo, haloalkyl, alkyl, alkoxy, haloalkoxy, hydroxy, cyano, nitro, amino, alkylamino and alkylthio;

$R^7$ and $R^8$ are each independently selected from hydrogen (H), alkyl, aryl and heteroaryl;

including all prodrug esters, pharmaceutically acceptable salts or stereoisomers thereof.

[2] In a preferred embodiment, the present invention provides a compound of formula I, wherein:

X is alkylene;

J is sulfur (S);

$R^1$ and $R^2$ are methyl, or $R^1$ is cyclized with $R^2$ to form a cyclopropyl ring;

$R^3$ is hydrogen;

z is 2;

Q is substituted or unsubstituted phenyl or naphthyl, or G;

$R^4$, $R^5$ and $R^6$ are hydrogen; and $R^7$ and $R^8$ are hydrogen.

[3] In a more preferred embodiment, the present invention provides a compound of formula I, wherein the compound is selected from:

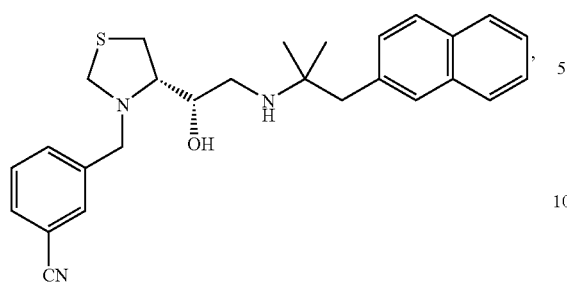
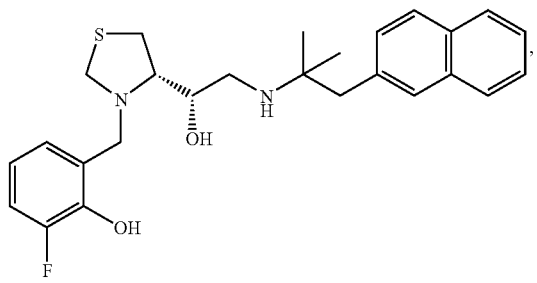
-continued
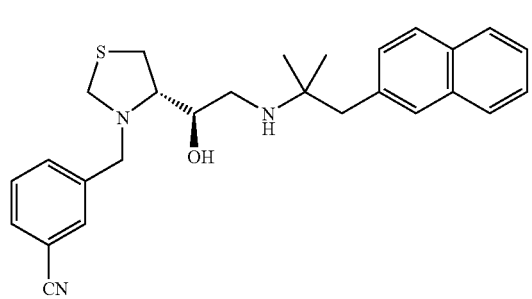
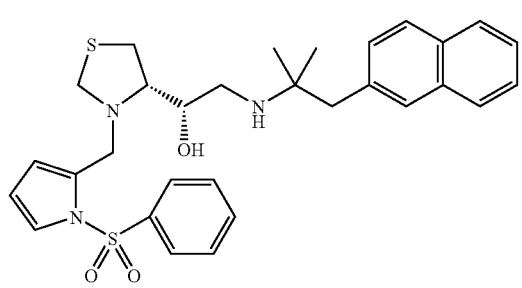
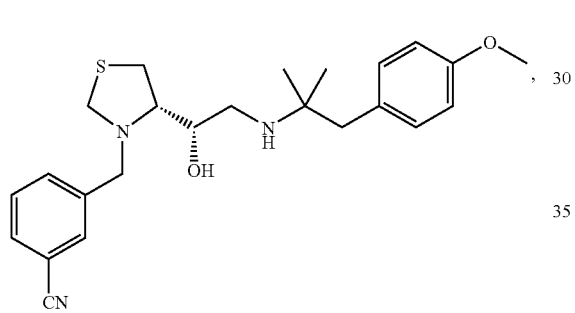
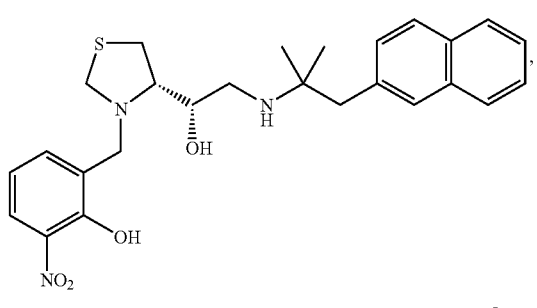
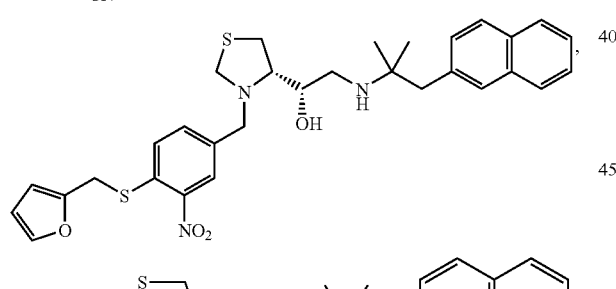
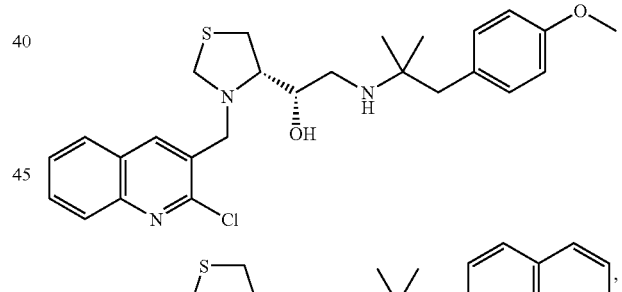
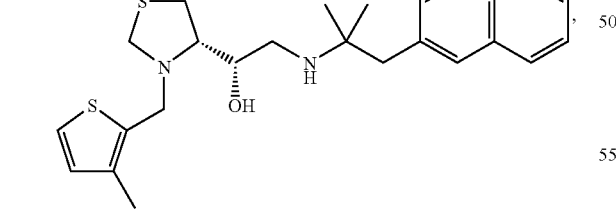
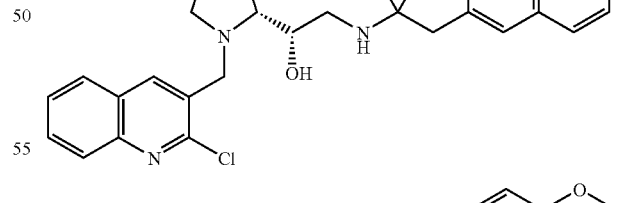
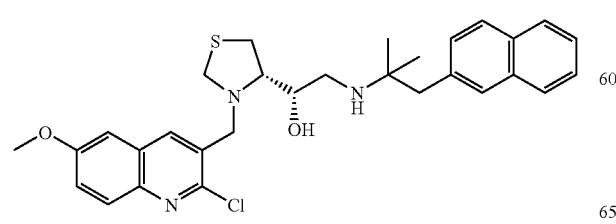
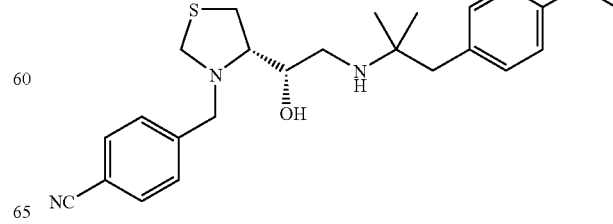

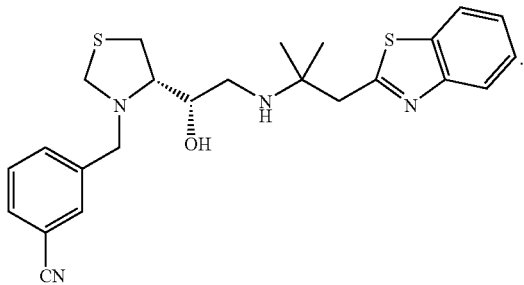

[4] In another more preferred embodiment, the present invention provides a compound of formula I wherein the compound is selected from:

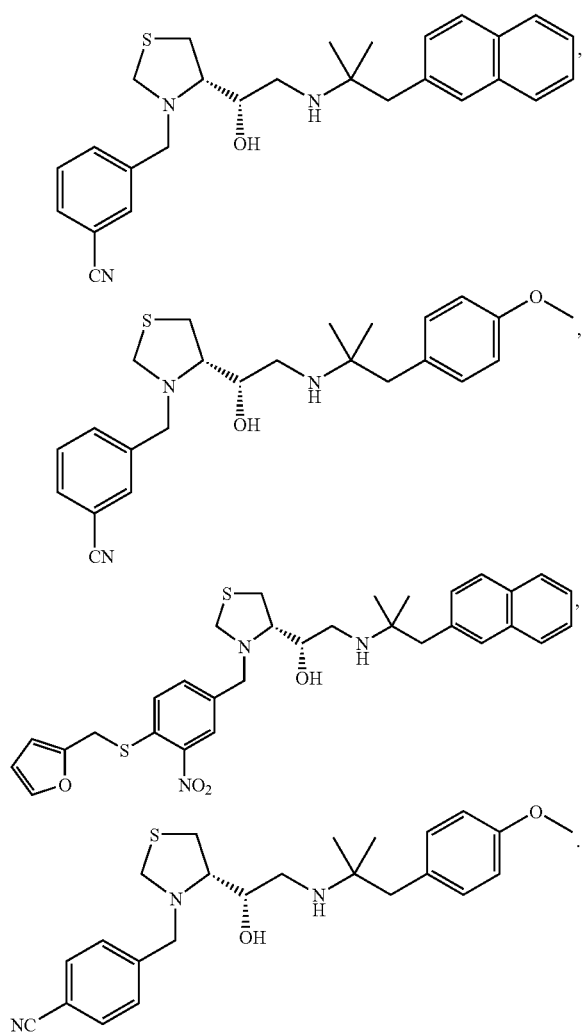

[5] In a second embodiment, the present invention provides a pharmaceutical composition comprising a compound of formula I as defined above and a pharmaceutically acceptable carrier therefor.

[6] In a preferred embodiment, the present invention provides a pharmaceutical composition as defined above further comprising at least one additional therapeutic agent selected from other compounds of formula I, anti-osteoporosis agents, cholesterol/lipid lowering agents, growth promoting agents, progesterone receptor agonists, modulators of bone resorption, selective estrogen receptor modulators, selective androgen receptor modulators, anti-resorptive agents, hormone replacement therapies, vitamin D, vitamin D analogues, elemental calcium, calcium supplements, cathepsin K inhibitors, MMP inhibitors, vitronectin receptor antagonists, Src SH$_2$ antagonists, Src kinase inhibitors, vacuolar H$^+$-ATPase inhibitors, PTH, PTH analogues and fragments, osteoprotegrin, Tibolone, p38 inhibitors, prostanoids, PPAR gamma antagonists and isoflavinoids.

[7] In a third embodiment, the present invention provides a method for treating or delaying the progression or onset of hypoparathyroidism, osteosarcoma, chondrosarcoma, periodontal disease, fracture healing, osteoarthritis, Paget's disease, osteopenia, glucocorticoid induced osteoporosis, osteomalacia, osteoporosis, metastatic bone disease or joint replacement, which comprises administering to a mammalian species in need of treatment a therapeutically effective amount of a compound of formula I as defined agove.

[8] In a preferred embodiment, the present invention provides a method as defined above further comprising administering, concurrently or sequentially, a therapeutically effective amount of at least one additional therapeutic agent selected from other compounds of formula I, anti-osteoporosis agents, cholesterol/lipid lowering agents, growth promoting agents, progesterone receptor agonists, modulators of bone resorption, selective estrogen receptor modulators, selective androgen receptor modulators, anti-resorptive agents, hormone replacement therapies, vitamin D, vitamin D analogues, elemental calcium, calcium supplements, cathepsin K inhibitors, MMP inhibitors, vitronectin receptor antagonists, Src SH$_2$ antagonists, Src kinase inhibitors, vacuolar H$^+$-ATPase inhibitors, PTH, PTH analogues and fragments, osteoprotegrin, Tibolone, p38 inhibitors, prostanoids, PPAR gamma antagonists and isoflavinoids.

[9] In a preferred embodiment, the present invention provides a method of enhancing bone formation in a mammalian species comprising administering a therapeutically effective amount of a compound of formula I as defined above to a patient in need thereof.

[10] In a fourth embodiment, the present invention provides a pharmaceutical composition capable of modulating the calcium sensing receptor comprising a compound of formula I

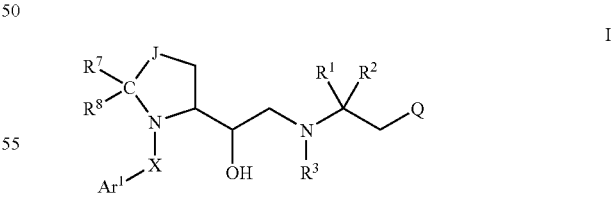

wherein
Ar$^1$ is a substituted or unsubstituted aryl or substituted or unsubstituted heteroaryl;
X is a linking group selected from alkylene, CO, alkyleneCO, OCO, alkyleneOCO, SO$_2$ and alkyleneSO$_2$;
J is a linking group selected from S, SO and SO$_2$;
R$^1$ and R$^2$ are each independently substituted or unsubstituted C$_1$–C$_4$ alkyl, or R$^1$ can be cyclized with R$^2$ to form (—CH$_2$—)$_m$ where m is an integer from 2 to 5;

$R^3$ is hydrogen (H) or alkyl;

Q is $Ar^1$ or G;

G is

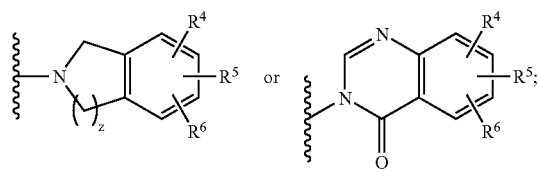

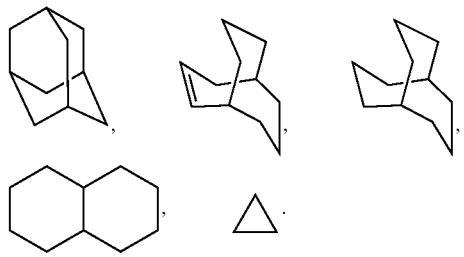

z is 1 or 2;

$R^4$, $R^5$ and $R^6$ are each independently selected from hydrogen (H), halo, haloalkyl, alkyl, alkoxy, haloalkoxy, hydroxy, cyano, nitro, amino, alkylamino and alkylthio;

$R^7$ and $R^8$ are each independently selected from hydrogen (H), alkyl, aryl and heteroaryl;

including all prodrug esters, pharmaceutically acceptable salts or stereoisomers thereof.

[11] In a preferred embodiment, the present invention provides a pharmaceutical composition as defined above wherein said composition is a calcium sensing receptor antagonist.

The following definitions apply to the terms as used throughout this specification, unless otherwise limited in specific instances.

The term "alkyl" or "lower alkyl" as employed herein, alone or as part of another group, includes both straight and branched chain hydrocarbons, containing 1 to 12 carbons, preferably 1 to 8 carbons, more preferably 1 to 4 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like. As defined and claimed herein, the term "alkyl" includes alkyl groups as defined above optionally substituted with one or more substituents commonly attached to such chains, such as, but not limited to halo, for example F, Br, Cl or I or $CF_3$, alkyl, alkoxy, aryl, aryloxy, aryl(aryl) or diaryl, arylalkyl, arylalkyloxy, alkenyl, alkynyl, cycloalkyl, cycloalkenyl, cycloalkylalkyl, cycloalkylalkyloxy, optionally substituted amino, hydroxy, hydroxyalkyl, acyl, oxo, alkanoyl, heteroaryl, heteroaryloxy, cycloheteroalkyl, arylheteroaryl, arylalkoxycarbonyl, heteroarylalkyl, heteroarylalkoxy, aryloxyalkyl, aryloxyaryl, alkylamido, alkanoylamino, arylcarbonylamino, alkoxycarbonyl, alkylaminocarbonyl, nitro, cyano, thiol, haloalkyl, trihaloalkyl, alkylthio, carboxyl, and the like.

Unless otherwise indicated, the term "cycloalkyl" as employed herein alone or as part of another group includes saturated or partially unsaturated (containing 1 or more double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl,

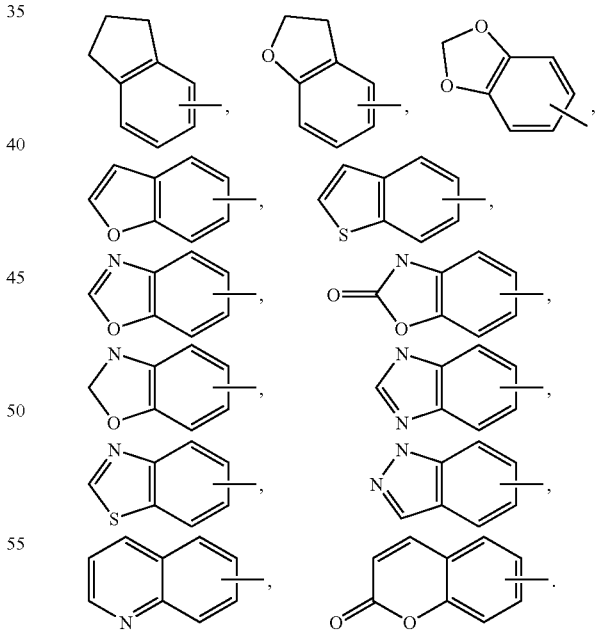

As defined and claimed herein, the term "cycloalkyl" includes cycloalkyl groups as defined above optionally substituted with 1 or more substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol and/or alkylthio and/or any of the substituents included in the definition of "substituted alkyl."

The term "halogen" or "halo" as used herein alone or as part of another group refers to chlorine, bromine, fluorine, and iodine.

Unless otherwise indicated, the term "aryl", "aromatic" or "Ar" as employed herein alone or as part of another group refers to monocyclic and polycyclic (conjugated or fused) aromatic groups containing 5 to 14 carbons in the ring portion (such as phenyl or naphthyl, including 1-naphthyl and 2-naphthyl) and may optionally include one to three additional rings fused to a carbocyclic ring or a heterocyclic ring (such as aryl, cycloalkyl, heteroaryl or cycloheteroalkyl rings, for example As defined and claimed herein, the term "aryl" includes aryl groups as defined above optionally substituted through available carbon atoms with one or more substitutents, such as hydrogen, halo, haloalkyl, alkyl, alkoxy, haloalkoxy, alkenyl, trifluoromethyl, trifluoromethoxy, alkynyl, cycloalkylalkyl, cycloheteroalkyl, cycloheteroalkylalkyl, aryl, heteroaryl, arylalkyl, heteroarylalkyl, aryloxy, aryloxyalkyl, alkoxyalkyl, arylalkoxy, alkoxycarbonyl, aryloxycarbonyl, arylalkoxycarbonyl, arylalkenyl, heteroarylalkenyl, heteroarylheteroaryl, heteroaryloxy, heteroarylalkoxy, heteroaryloxyalkyl, aminocarbonylalkyl, aminocarbonylaryl, arylthio, arylalkylthio, heteroarylalkylthio, arylazo, hydroxy, nitro, cyano, carboxyl, carboxylalkoxy, alkoxycarbonylalkoxy, amino, substituted amino, wherein the amino includes 1 or 2 substituents such as alkyl, aryl (or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, alkylsulfonyl, arylsulfonyl, heteroarylsulfonyl, cycloheteroalkylsulfonyl, alkylsulfinyl, arylsulfinyl, arylsulfinylalkyl, arylsulfonylamino, arylsulfonaminocarbonyl and/or any of the alkyl substituents set out herein.

The term "fused" refers to aromatic or heteroaromatic rings that share a pair of carbon atoms, and includes multiple fused aromatic or heteroaromatic rings, for example naphthalene or naphthyridine.

Unless otherwise indicated, the term "heteroaryl" or "heteroaromatic" as used herein alone or as part of another group refers to a 5- or 6-membered aromatic ring which includes 1, 2, 3 or 4 hetero atoms such as nitrogen, oxygen, or sulfur, and such rings fused to an aryl, cycloalkyl, heteroaryl or cycloheteroalkyl ring (e.g. benzothiophenyl, indole), and includes possible N-oxides. As defined and claimed herein, the term "heteroaryl" or "heteroaromatic" includes heteroaryl groups as defined above optionally substituted through any available carbon atoms with one or more substituents such as any of the alkyl or aryl substituents set out above. Examples of heteroaryl groups include the following:

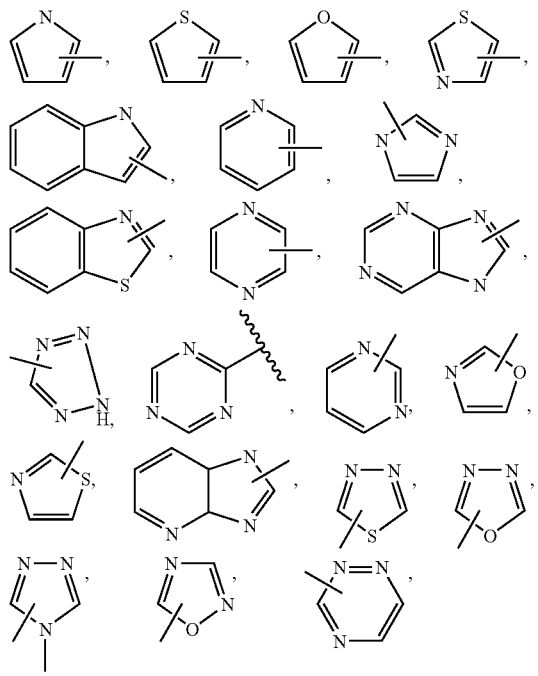

and the like.

Unless otherwise indicated, the term "alkoxy", "aryloxy" or "arylalkoxy" as employed herein alone or as part of another group includes any of the above alkyl, arylalkyl or aryl groups linked to an oxygen atom.

Unless otherwise indicated, the term "alkylthio" or "arylthio" as employed herein alone or as part of another group includes any of the above alkyl, arylalkyl or aryl groups linked through a sulfur atom.

Unless otherwise indicated, the term "alkylamino" or "arylamino" as employed herein alone or as part of another group includes any of the above alkyl, aryl or arylalkyl groups linked through a nitrogen atom.

Unless otherwise indicated, the term "haloalkyl" or "haloalkoxy" as employed herein alone or as part of another group includes a halo group, linked through an alkyl group or alkoxy group, respectively.

The term "cyano," as used herein, refers to a —CN group.
The term "carboxyl" denotes —C(O)O—.
The term "nitro" as used herein, refers to a —NO$_2$ group.
The term "hydroxy" as used herein, refers to —OH.
The term "amino" refers to a group of the formula —NZ$_1$Z$_2$ wherein Z$_1$ and Z$_2$ are each hydrogen, or Z$_1$ and Z$_2$ may each independently be alkyl, aryl or any of the substituents described for substituted alkyl or substituted aryl above.

The compounds of formula I can be present as salts, which are also within the scope of this invention. Pharmaceutically acceptable (i.e., non-toxic, physiologically acceptable) salts are preferred. If the compounds of formula I have, for example, at least one basic center, they can form acid addition salts. These are formed, for example, with strong inorganic acids, such as mineral acids, for example sulfuric acid, phosphoric acid or a hydrohalic acid, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as (C$_1$–C$_4$) alkyl or arylsulfonic acids which are unsubstituted or substituted, for example by halogen, for example methyl- or p-toluenesulfonic acid. Corresponding acid addition salts can also be formed having, if desired, an additionally present basic center. The compounds of formula I having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di- or tri-lower alkylamine, for example ethyl, tertbutyl, diethyl, diisopropyl, triethyl, tributyl or dimethylpropylamine, or a mono-, di- or trihydroxy lower alkylamine, for example mono-, di- or triethanolamine. Corresponding internal salts may furthermore be formed. Salts which are unsuitable for pharmaceutical uses but which can be employed, for example, for the isolation or purification of free compounds of formula I or their pharmaceutically acceptable salts, are also included.

Preferred salts of the compounds of formula I which contain a basic group include monohydrochloride, hydrogen sulfate, methanesulfonate, phosphate or nitrate.

Preferred salts of the compounds of formula I which contain an acid group include sodium, potassium and magnesium salts and pharmaceutically acceptable organic amines.

The term "modulator" refers to a chemical compound with capacity to either enhance (e.g., "agonist" activity) or inhibit (e.g., "antagonist" activity) a functional property of biological activity or process (e.g., enzyme activity or receptor binding); such enhancement or inhibition may be contingent on the occurrence of a specific event, such as activation of a signal transduction pathway, and/or may be manifest only in particular cell types.

The term "prodrug esters" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates and the like.

Any compound that can be converted in vivo to provide the bioactive agent (i.e., the compound of formula I) is a prodrug within the scope and spirit of the invention.

Various forms of prodrugs are well known in the art. A comprehensive description of prodrugs and prodrug derivatives are described in:

*The Practice of Medicinal Chemistry*, Camille G. Wermuth et al., Ch 31, (Academic Press, 1996);

*Design of Prodrugs*, edited by H. Bundgaard, (Elsevier, 1985); and

*A Textbook of Drug Design and Development*, P. Krogsgaard-Larson and H. Bundgaard, eds. Ch 5, pgs 113–191 (Harwood Academic Publishers, 1991).

Said references are incorporated herein by reference.

An administration of a therapeutic agent of the invention includes administration of a therapeutically effective amount of the agent of the invention. The term "therapeutically effective amount" as used herein refers to an amount of a therapeutic agent to treat or prevent a condition treatable by administration of a composition of the invention. That amount is the amount sufficient to exhibit a detectable therapeutic or preventative or ameliorative effect. The effect may include, for example, treatment or prevention of the conditions listed herein. The precise effective amount for a subject will depend upon the subject's size and health, the nature and extent of the condition being treated, recommendations of the treating physician, and the therapeutics or combination of therapeutics selected for administration. Thus, it is not useful to specify an exact effective amount in advance.

All stereoisomers of the compounds of the instant invention are contemplated, either in admixture or in pure or substantially pure form. The compounds of the present invention can have asymmetric centers at any of the carbon atoms including any one of the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatography or fractional crystallization.

The compounds of formula I of the invention can be prepared as shown in the following reaction schemes and description thereof, as well as relevant published literature procedures that may be used by one skilled in the art. Exemplary reagents and procedures for these reactions appear hereinafter and in the working Examples.

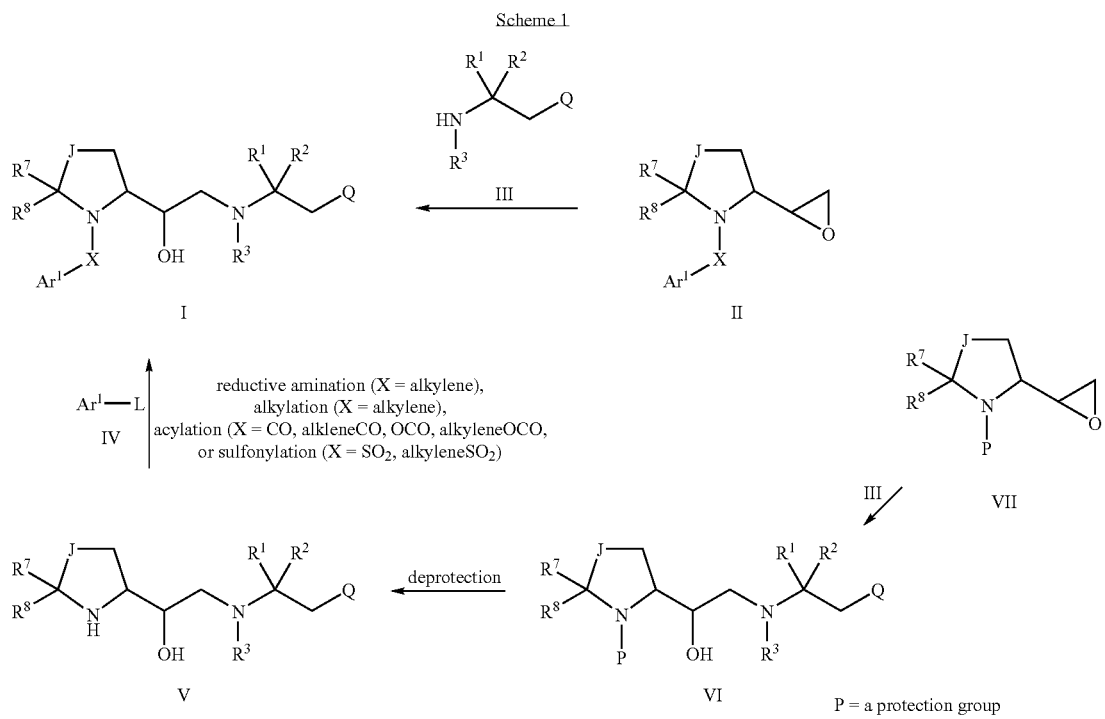

Compounds of formula I can be prepared from the N-functionalized epoxide II by coupling of the amine III, either by heating (e.g. between 50° C. and 120° C.) the mixture neat or, preferably, in an alcoholic solvent, such as ethanol or isopropanol. Alternatively, the unfunctionalized thiazolidine V can be reacted with the appropriate alkylating, acylating, or sulfonylating reagent to provide compounds of formula I. In cases where X represents an alkylene group, such compounds can be provided by reductive amination with the appropriate aldehyde and a reducing agent, such as sodium borohydride, sodium cyanoborohydride, or sodium triacetoxyborohydride, in a solvent such as methanol, THF, or DMF, or alkylation can be performed by reaction of the appropriate alkyl halide (Cl, Br, or I) and an inorganic or tertiary amine base, such as potassium carbonate or triethylamine, in a polar solvent such as DMF or acetonitrile. In cases where X represents a carbonyl group, such compounds can be provided by acylation with the appropriate acid halide, preferably in the presence of a tertiary amine base, such as triethylamine or N,N-diisopropylethylamine, in a solvent such as dichloromethane or chloroform, or the appropriate carboxylic acid can coupled through the reaction of standard acylation reagents such as 1-(3-dimethylaminopropyl)-3-ethylcarbodiimide (EDC) and 1-hydroxybenztriazole (HOBt), or bromotripyrrolidino- Theodora W.; Wuts, Peter G. M. *Protective Groups in Organic Synthesis*, 3$^{rd}$ ed.; Wiley & Sons: New York, 1999. Preferably, P is a carbamate protecting group, such as benzyloxycarbonyl (Cbz) or tert-butoxycarbonyl (BOC). The protected amine VI can be prepared from coupling of the epoxide VII and the amine III in a manner similar to that discussed above for the coupling of epoxide II and amine III.

Compounds described in Scheme 1 where J is sulfur(S) can be oxidized to the corresponding thiazolidine S-oxides according to standard methods known in the literature (e.g. Stewart, R. In *Oxidation in Organic Chemistry*; Wiberg, K. B., Ed.; Academic Press: New York, 1965; Lee, D. G. In Oxidation in *Oxydation in Organic Chemistry*; Trahanovsky, W. S., Ed.; Academic Press: New York, 1982; Arndt, D. In Methoden der Organischen Chemie (Houben-Weyl) 4$^{th}$ Ed.; Muller, E., E d., Thieme: Stuttgart, 1975; Vol. E 4/1b; and, Betts, M. J. J. *Chem. Soc., Perkin Trans.* 1, 1999, 1067–1072).

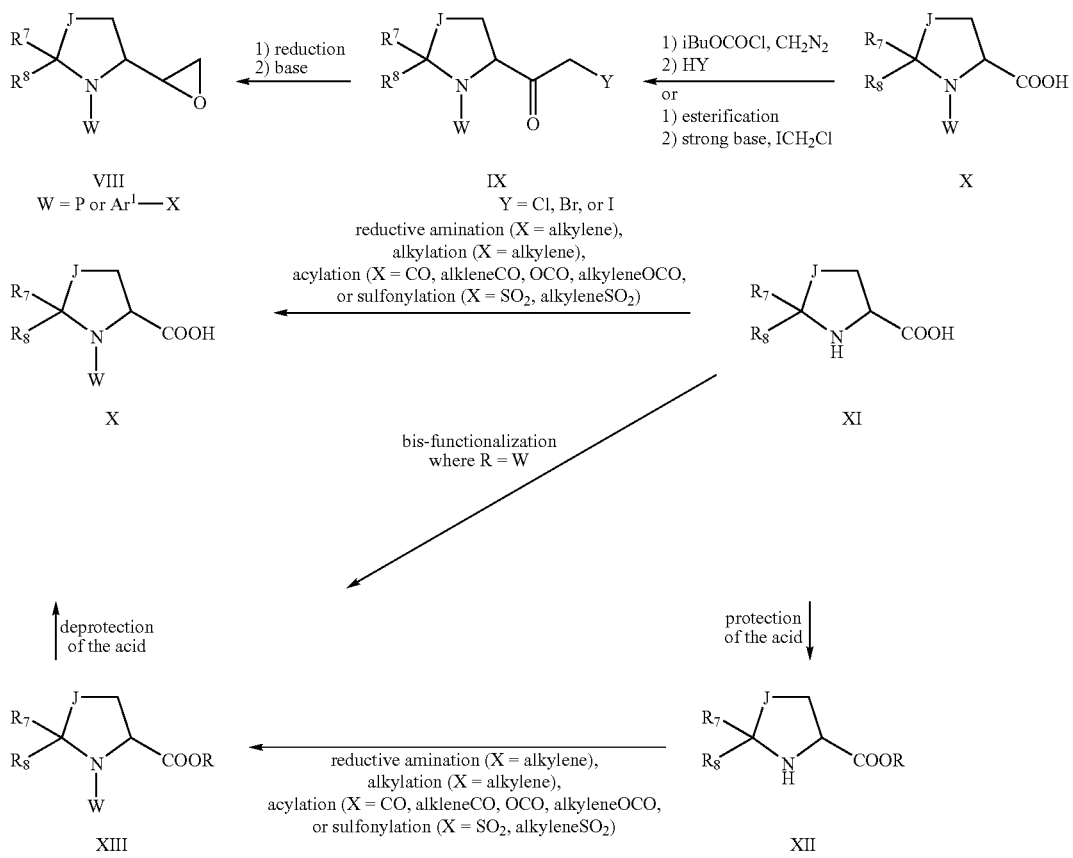

Scheme 2 phosphonium hexafluorophosphate (PyBroP) as known in the literature. In cases where X represents a sulfonyl group, such compounds can be provided by sulfonylation with the appropriate sulfonyl chloride, with or without a tertiary amine base such as triethylamine, in a solvent such as dichloromethane, but preferably in pyridine.

Compound V can be prepared from the protected thiazolidine, compound VI, where P is a protecting group. Suitable protecting groups or references thereto can be found, along with the appropriate deprotection conditions, in Greene, The intermediate epoxides II and VII can be prepared according to Scheme 2. Reduction of the carbonyl group of the halomethyl ketone IX, with a reagent such as sodium borohydride or L-selectride, preferably at a temperature between −78° C. and 0° C., in a solvent such as THF, followed by treatment with a base such as potassium hydroxide in methanol can provide compound VIII. The halomethyl ketone IX can be prepared from the corresponding carboxylic acid through reaction of an acylating agent, preferably a mixed anhydride, with diazomethane followed by treatment with the appropriate hydrogen halide; or, by esterification followed by treatment with the reagent formed by reaction of a strong base with chloroiodomethane.

The functionalized carboxylic acid X can be prepared by reacting the unfunctionalized amino acid XI with the appropriate alkylating, acylating or sulfonylating reagent (see Scheme 1). Alternatively, compound XI can be converted to a protected carboxylate XII (e.g. ester), which could be functionalized in a manner similar to preparation of compound X from compound XI, to provide compound XIII. Compound XIII could also arise from functionalization of both the amine and carboxylic acid groups of XI in one step. Selective deprotection of XIII could then provide compound X. Suitable protection and deprotection groups and conditions are well known in the aforementioned literature. The carboxylic acid starting materials XI are either commercially available, known in the literature, or can be prepared according to the synthesis of similar-analogs prepared in the literature (e.g. Greenstein, J. P. and Winitz, M. *Chemistry of the Amino Acids* vol. 3 (1986), and references herein).

pared from reaction of the appropriate ketene acetal with the acetate XVI. Preparation of IIIa is also possible via amination of the olefin XVII under Ritter conditions, such as through treatment with sodium cyanide, acetic acid, and sulfuric acid, followed by base hydrolysis of the intermediate amide. Wittig olefination of the appropriate aldehyde XVIII can provide olefin XVII. The starting materials XIV, XVI, and XVIII are either commercially available, known in the literature, or can be prepared according to the synthesis of similar analogs prepared in the literature.

Additional methods of preparation of compound III can be found in *Recl. Trav. Chim. Pays-Bas* 1955, 74,919; *J. Med. Chem.* 1982, 530; *J. Med. Chem.* 1986; 1406; *Bull. Soc. Chim. Fr.* 1943, 349; and, *Aust. J. Chem.* 1986, 39, 281.

Utilities & Combinations

A. Utilities

Diseases or disorders which can be treated by modulating calcium sensing receptor activity can be identified based on the functional responses of cells regulated by calcium recep-

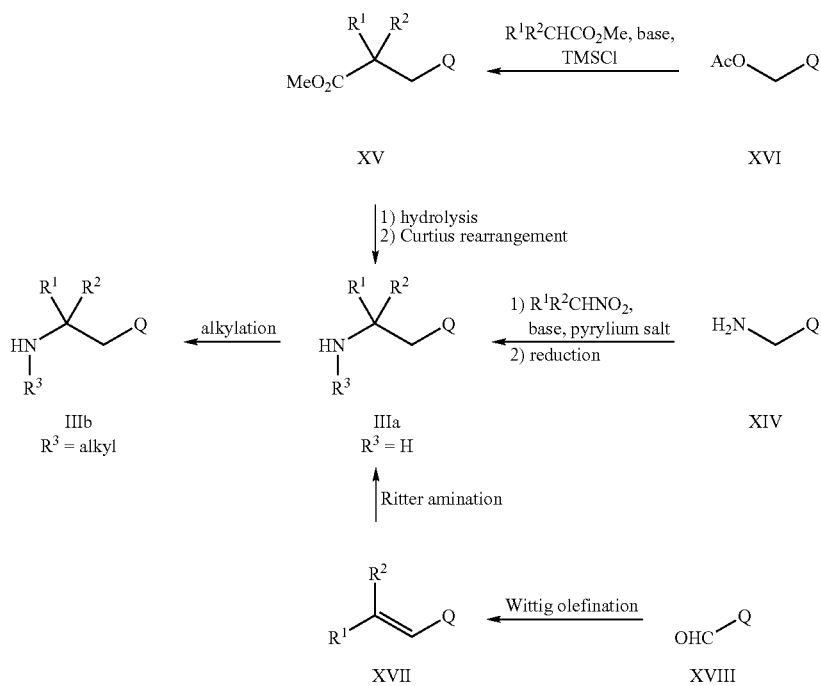

Preparation of intermediate III is provided in Scheme 3. Treatment of the appropriate primary amine XIV with a pyrylium salt, such as 2,4,6-triphenylpyrylium tetrafluoroborate, followed by reaction of an appropriately substituted nitroalkane in the presence of a strong base, such as sodium methoxide, provides an intermediate nitro compound, which can be reduced to the corresponding primary amine IIIa, for example, under reducing conditions such as hydrogen gas (at atmospheric pressure or up to 80 psig) over a Pd catalyst or Raney nickel, in a solvent such as methanol or ethyl acetate. Alternatively, IIIa can arise from ester XV via hydrolysis to the carboxylic acid (e.g. aqueous sodium hydroxide in methanol), followed by Curtius rearrangement, using for example diphenylphosphoryl azide and benzyl alcohol followed by hydrogenolysis. Ester XV can be pretor activity. Functional responses of cells regulated by the calcium sensing receptor are known in the art, including parathyroid hormone ("PTH") secretion by parathyroid cells, calcitonin secretion by C-cells, bone reabsorption by osteoclasts and $Ca^{2+}$ secretion by kidney cells.

The compounds of the present invention preferably function as modulators of the calcium sensing receptor, particularly as antagonists of the calcium sensing receptor. Accordingly, the compounds of the invention may be used to stimulate a functional response by parathyroid cells whereby such cells release PTH, preferably a transient release of PTH. Thus, the compounds of the present invention may be used in the treatment of diseases or disorders which can be affected by modulating one or more activities or functions of a calcium sensing receptor, wherein treatment comprises prevention, partial alleviation or cure of the condition or disorder. Modulation may occur locally, for example with certain tissues of the subject, or more extensively throughout a subject being treated for such a condition or disorder.

The compounds of the present invention can be administered animals, including humans, for the treatment of a variety of conditions and disorders, including, but not limited to bone and mineral-related diseases or disorders, (e.g., hypoparathyroidism, osteosarcoma, chondrosarcoma, periodontal disease, fracture healing, osteoarthritis, Paget's disease, osteopenia, glucocorticoid induced osteoporosis, osteomalacia and osteoporosis); metastatic bone disease; joint replacement; diseases involving excess water reabsorption by the kidney, such as syndrome of inappropriate ADA secretion (SIADH), cirrhosis, congestive heart failure and nephrosis; hypertension; diseases involving abnormally low serum parathyroid levels; preventing and/or decreasing renal toxicity from cationic antibiotics (e.g., amionglycoside antibiotics); renal osteodystrophy; gut motility disorders, such as diarrhea and spastic colon, GI ulcer diseases; GI diseases with excessive calcium absorption; sarcoidosis; autoimmune diseases and organ transplant rejection; inflammatory diseases, such as ashthma, rheumatoid arthritis, inflammatory bowel disease, transplant rejection, and chronic obstructive pulmonary disease; and diseases caused by excess gastric acid secretion.

B. Combinations

The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other compounds of the invention, or in combination with one or more other therapeutic agent(s) or other pharmaceutically active materials.

The compounds of the present invention may be employed in combination with other modulators of the calcium sensing receptor or other suitable therapeutic agents useful in the treatment of the aforementioned disorders including anti-osteoporosis agents, cholesterol/lipid lowering agents, growth promoting agents and/or progesterone receptor agonists.

Examples of suitable anti-osteoporosis agents for use in combination with the compounds of the present invention include bisphosphonates (e.g., alendronate, risedronate, ibandronate and zolendrate) parathyroid hormone, PTH fragment, calcitonins, RANK ligand antagonists, TRAP inhibitors and AP-1 inhibitors.

Examples of suitable cholesterol/lipid lowering agents for use in combination with the compounds of the present invention include HMG-CoA reductase inhibitors (e.g., pravastatin, lovastatin, atorvastatin, simvastatin, NK-104 (a.k.a. itavastatin, or nisvastatin or nisbastatin) and ZD-4522 (a.k.a. rosuvastatin, or atavastatin or visastatin)).

Examples of suitable growth promoting agents for use in combination with the compounds of the present invention include growth hormone secretagogues, such as GHRP-6, GHRP-1 (as described in U.S. Pat. No. 4,411,890 and publications WO 89/07110 and WO 89/07111), GHRP-2 (as described in WO 93/04081), NN703 (Novo Nordisk), LY444711 (Lilly), MK-677 (Merck), CP424391 (Pfizer) and B-HT920, or with growth hormone releasing factor and its analogs or growth hormone and its analogs or somatomedins including IGF-1 and IGF-2, or with alpha-adrenergic agonists, such as clonidine or serotonin 5-$HT_{1D}$ agonists, such as sumatriptan, or agents which inhibit somatostatin or its release, such as physostigmine and pyridostigmine.

Examples of suitable progesterone receptor agonists for use in combination with the compounds of the present invention include levonorgestrel and medroxyprogesterone acetate (MPA).

The compounds of the present invention may further be used in combination with modulators of bone resorption (e.g., estrogen); selective estrogen receptor modulators (e.g., tamoxifen, lasofoxifene, TSE-424 and raloxifene); or selective androgen receptor modulators, such as those disclosed in Edwards, J. P. et al., *Bio. Med. Chem. Let.*, 9, 1003–1008 (1999) and Hamann, L. G. et al., *J. Med. Chem.*, 42, 210–212 (1999).

In addition, compounds of the present invention may be used in combination with therapeutic agents such as anti-resorptive agents; hormone replacement therapies; vitamin D and analogues thereof (e.g., 1,25-dihydroxy vitamin D3); elemental calcium and calcium supplements; cathepsin K inhibitors; MMP inhibitors; vitronectin receptor antagonists; Src $SH_2$ antagonists; Src kinase inhibitors; vacuolar $H^+$-ATPase inhibitors; PTH and its analogues and fragments; osteoprotegrin; Tibolone; p38 inhibitors; prostanoids; PPAR gamma antagonists or isoflavinoids (e.g., genistein, iprifavone and testosterone).

The above other therapeutic agents, when employed in combination with the compounds of the present invention, may be used, for example, in those amounts indicated in the Physicians' Desk Reference (PDR) or as otherwise determined by one of ordinary skill in the art.

The compounds of the formula I can be administered for any of the uses described herein by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The compounds of formula I can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxypropyl cellulose (HPC), hydroxypropyl methyl cellulose (HPMC), sodium carboxymethyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use.

Exemplary compositions for nasal, aerosol, or inhalation administration include solutions in saline which can contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for rectal administration include suppositories which can contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

The effective amount of a compound of the present invention can be determined by one of ordinary skill in the art, and includes exemplary dosage amounts for a adult human of from about 0.001 to 100 mg/kg of body weight of active compound per day, preferably 0.01 to 1 mg/kg of body weight of active compound per day, that can be administered in a single dose or in the form of individual divided doses, such as from 1 to 4 times per day. It will be understood that the specific dose level and frequency of dosage for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to NHR-associated conditions.

The following examples serve to better illustrate, but not limit, some of the preferred embodiments of the invention.

The following abbreviations are employed in the Examples:

AcOEt=ethyl acetate
AcOH=acetic acid
aq.=aqueous
Ar=argon
Bn=benzyl
BOC=tert-butoxycarbonyl
BOP reagent=benzotriazol-1-yloxy-tris(dimethylamino) phosphonium hexafluorophosphate
br=broad
Bu=butyl
c=concentration
° C.=degrees Centigrade
CAN=ceric ammonium nitrate
CBZ=carbobenzyloxy or carbobenzoxy or benzyloxycarbonyl
$CDCl_3$=chloroform-d
$CD_3OD$=methanol-$d_4$
$CH_2Cl_2$=dichloromethane
$CHCl_3$=chloroform
$Cs_2CO_3$=cesium carbonate
d=doublet
DBU=1,8-diazabicyclo[5.4.0]undec-7-ene
DEAD=diethylazodicarboxylate
DIAD=diisopropylazodicarboxylate
DIBAL=diisobutylaluminum hydride
DMAP=4-dimethylaminopyridine
DME=1,2-dimethoxyethane
DMF=dimethylformamide
DMSO=dimethylsulfoxide
EDC=3-ethyl-3'-(dimethylamino)propylcarbodiimide hydrochloride
ES+=electrospray positive ionization
Et=ethyl
$Et_3N$=triethylamine
EtOAc=ethyl acetate
$Et_2O$=diethyl ether
EtOH=ethanol
FMOC=fluorenylmethoxycarbonyl
g=gram(s)
h=hour(s)
HCl=hydrochloric acid
hex=hexane or hexanes
$HNO_3$=nitric acid
$H_2O$=water
HOAc=acetic acid
HOAT=1-hydroxy-7-azabenzotriazole
HOBT=1-hydroxybenzotriazole hydrate
HPLC=high performance liquid chromatography
$H_3PO_4$=phosphoric acid
$H_2SO_4$=sulfuric acid
Hz=hertz
iPr=isopropyl
$iPr_2NEt$=diisopropylethylamine
iPrOH=isopropanol
$K_2CO_3$=potassium carbonate
KF=potassium fluoride
KHMDS=potassium bis(trimethylsilyl)amide
$KHSO_4$ potassium hydrogen sulfate
KOH=potassium hydroxide
L=liter(s)
LAH=lithium aluminum hydride
LC/MS=high performance liquid chromatography/mass spectrometry
$LiAlH_4$=lithium aluminum hydride
LiHMDS=lithium bis(trimethylsilyl)amide
LiOH=lithium hydroxide
m=multiplet
M=molar
mCPBA=3-chloroperoxybenzoic acid
Me=methyl
MeOH=methanol
meq=milliequivalent(s)
mg=milligram(s)
$MgSO_4$=magnesium sulfate
MHz=megahertz
μL=microliter(s)
min=minute(s)

mL=milliliter(s)
mm=millimeter(s)
mmol=millimole(s)
MnO₂=manganese dioxide
mol=mole(s)
mp=melting point
MS or Mass Spec=mass spectrometry
m/z=mass to charge ratio
N₂=nitrogen
NaBH₄=sodium borohydride
NaBH(OAc)₃=sodium triacetoxyborohydride
NaCNBH₃=sodium cyanoborohydride
NaHCO₃=sodium bicarbonate
NaHMDS=sodium bis(trimethylsilyl)amide
NaOH=sodium hydroxide
NaOMe=sodium methoxide
Na₂SO₄=sodium sulfate
nBuLi=n-butyllithium
NH₄OH=ammonium hydroxide
NMM=N-methylmorpholine
NMO=N-methylmorpholine N-oxide
NMR=nuclear magnetic resonance
Pd/C=palladium on carbon
Pd(OAc)₂=Palladium acetate
Ph=phenyl
Ph₃P=triphenylphosphine
(Ph₃P)₄Pd=tetrakistriphenylphosphine palladium
P₂O₅=phosphorus pentoxide
POCl₃=phosphorus oxychloride
Pr=propyl
PtO₂=platinum oxide
RT=room temperature
s=singlet
sat or sat'd=saturated
t=triplet
TBS=tert-butyldimethylsilyl
tBu=tertiary butyl
TFA=trifluoroacetic acid
THF=tetrahydrofuran
Ti(OiPr)₄=titanium isopropoxide
TLC=thin layer chromatography
TMS=trimethylsilyl or trimethylsilane
UV=ultraviolet HPLC analysis of the exemplified compounds was carried out under one of the following reverse phase methods, with the appropriate method and retention time noted in the Examples.

Method A: YMC S5 ODS 4.6×50 mm column, gradient elution 0–100% B/A over 4 min (solvent A=10% MeOH/H₂O containing 0.2% H₃PO₄, solvent B=90% MeOH/H₂O containing 0.2% H₃PO₄), flow rate 4 mL/min, UV detection at 220 nm.

Method B: Zorbax SB C18 4.6×75 mm column, gradient elution 0–100% B/A over 8 min (solvent A=10% MeOH/H₂O containing 0.2% H₃PO₄, solvent B=90% MeOH/H₂O containing 0.2% H₃PO₄), flow rate 2.5 mL/min, UV detection at 220 nm.

Method C: Phenomenex S5 ODS 4.6×50 mm column, gradient elution 0–100% B/A over 4 min (solvent A=10% MeOH/H₂O containing 0.1% TFA, solvent B=90% MeOH/H₂O containing 0.1% TFA), flow rate 4 mL/min, UV detection at 220 nm.

Preparation of Intermediates

Preparation 1

3-(4-Oxiranyl-thiazolidin-3-ylmethyl)-benzonitriles

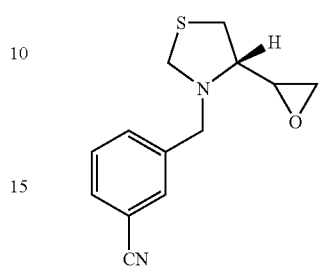

A. Preparation of 3-(3-cyano-benzyl)-thiazolidine-4-carboxylic acid 3-cyano-benzyl ester

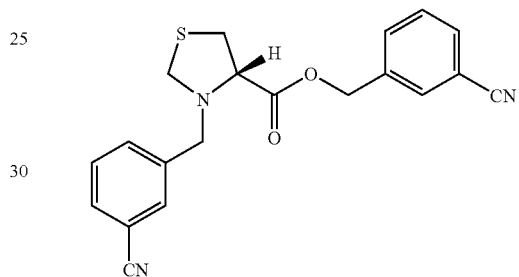

A mixture of D-thiazolidine-4-carboxylic acid (2 g, 15 mmol), K₂CO₃ (4.16 g, 30 mmol) and 3-(bromomethyl)benzonitrile (5.9 g, 30.1 mmol) in DMF (24 mL) was stirred at 90° C. for 30 min. Upon cooling to room temperature, ethyl acetate (300 mL) was added and the mixture was washed with water (2×100 mL) and brine (2×100 mL), then dried over MgSO₄ and concentrated. The crude compound was purified by flash chromatography on silica gel eluting with 30% AcOEt/hexane to give the title compound (3.65 g, 67%) as a colorless oil.

¹H NMR (400 MHz, CDCl₃): δ 3.26–3.32 (m, 2H); 3.71 (d, 1H, J=14 Hz); 3.79 (d, 1H, J=14 Hz); 3.98 (d, 1H, J=9.7 Hz); 4.15 (m, 1H); 4.22 (d, 1H, J=9.7 Hz); 5.20 (q, 2H, J=15.6 and 12.9 Hz); 7.47–7.73 (m, 8H).

B. Preparation of 3-(3-cyano-benzyl)-thiazolidine-4-carboxylic acid

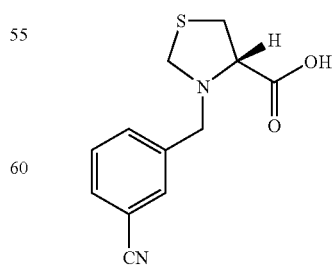

To a solution of the Part A compound (3.65 g, 10 mmol) in THF/MeOH (1:1, 10 mL), was added 4N aqueous NaOH solution (10 mL). The reaction was stirred for 1 h at room temperature, the pH was adjusted to 6 with AcOH, and the resulting mixture was extracted with AcOEt (3×15 mL). The combined organic phases were washed with brine and dried over MgSO$_4$. Concentration to dryness yielded an oil which was purified by flash chromatography on silica gel, loading with CH$_2$Cl$_2$ and eluting with 5% MeOH/CH$_2$Cl$_2$ to give the title compound (1.85 g, 75%) as a colorless oil.

$^1$H NMR (500 MHz, CDCl$_3$): δ 3.25 (q, 1H, J=10 Hz); 3.36 (q, 1H, J=5 Hz); 3.71 (d, 1H, J=15 Hz); 3.79 (d, 1H, J=15 Hz); 3.93 (d, 1H, J=10 Hz); 4.05 (q, 1H); 4.19 (d, 1H, J=10 Hz), 7.45 (t, 1H, J=5 Hz); 7.58 (d, 1H, J=5 Hz); 7.63 (d, 1H, J=5 Hz); 7.72 (s, 1H); 8.64 (broad).

C. Preparation of 3-[4-(2-chloro-acetyl)-thiazolidin-3-ylmethyl]-benzonitrile

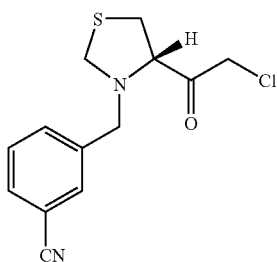

Diazomethane preparation: To a cold mixture of KOH solution (4 g in 9 mL water) and Et$_2$O (40 mL) at 0° C. was slowly added MNNG (1-methyl-3-nitro-1-nitrosoguanidine) (3.5 g, 24.2 mmol) in portions. Gas was evolved. This bi-phasic mixture was kept at 0° C. until no more gas evolved. The yellow ether layer was decanted into a dry flask and kept at 0° C. ready to use in the next reaction.

To a solution of the Part B compound (1.5 g, 6.05 mmol) and triethylamine (1 mL, 7.28 mmol) in THF (20 mL) at −10° C. (ice in acetone) was added dropwise isobutylchloroformate (0.8 mL, 6.05 mmol). The reaction was stirred at −10° C. for 30 min. The resulting white precipitate was filtered, and the filtrate was maintained at −10° C. To this solution was added the solution of diazomethane in ether prepared above. The reaction was stirred at −10° C. for 1 h. The volatiles were evaporated. Ethyl acetate was added and the solution was washed with H$_2$O, saturated NaHCO$_3$ solution, and brine, then dried over MgSO$_4$. Evaporation of the solvent gave a yellow oil. Purification was performed by flash chromatography on silica gel, loading with CH$_2$Cl$_2$ and eluting with 25% ethyl acetate in hexane. Pure fractions were combined and evaporated to give the diazomethyl ketone (1.1 g, 67%) as a pale yellow oil.

$^1$H NMR (400 MHz, CDCl$_3$): δ 3.07 (m, 1H); 3.65–3.8 (m, 3H); 3.9 (d, 2H); 4.01 (d, 1H); 5.99 (s, 1H); 7.49 (t, 1H, J=7.6 Hz); 7.60–7.64 (m, 2H); 7.73 (s, 1H).

To a solution of the diazo compound prepared above (1.1 g, 4.04 mmol) in CH$_2$Cl$_2$ (25 mL) at −10° C., was added 4N HCl in dioxane (2 mL) dropwise. Gas was evolved and the reaction was stirred at −10° C. for 1 h, then evaporated to dryness. AcOEt (10 mL) was added and the solution was washed with saturated sodium bicarbonate solution and brine. The organic phase was dried over MgSO$_4$ and evaporated to give the title compound (0.88 g, 78% yield) as a yellow oil.

$^1$H NMR (400 MHz, CDCl$_3$): δ 2.97 (q, 1H, J=3.8 Hz); 3.5 (q, 1H, J=2.1 Hz); 3.65–3.85 (m, 4H); 4.15 (d, 1H); 4.34 (q, 2H), 7.45 (t, 1H, J=7.5 Hz); 7.55 (d, 1H, J=7.5 Hz); 7.6 (d, 1H, J=8.1 Hz); 7.66 (s, 1H).

D. Preparation of 3-(4-oxiranyl-thiazolidin-3-ylmethyl)-benzonitrile

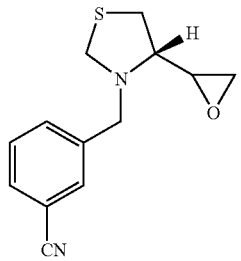

To a cooled solution (0° C.) of the Part C compound (780 mg 2.78 mmol) in MeOH/THF (1:1, 10 mL) was added NaBH$_4$ (105 mg, 2.78 mmol). The mixture was stirred at 0° C. for 30 min then at 1 h at room temperature. The reaction mixture was quenched with AcOH. AcOEt (20 mL) was added and the solution was washed with a saturated sodium bicarbonate solution and brine. The organic phase was dried over MgSO$_4$ and evaporated to give 680 mg of a crude oil. Purification by flash chromatography on silica gel, loading with CH$_2$Cl$_2$ and eluting with 30% AcOEt/Hexane gave the title compound (420 mg, 71%) as mixture of the two diastereomers. Further separation was performed by preparative reverse phase HPLC.

Diastereomer A:
MS (ES+) m/z 247.3 [M+H]$^+$.
HPLC retention time=1.89 min (Method C).

Diastereomer B:
MS (ES+) m/z 247.3 [M+H]$^+$.
HPLC retention time=2.14 min (Method C).

Preparation 2

4-Oxiranyl-thiazolidine-3-carboxylic acid tert-butyl esters

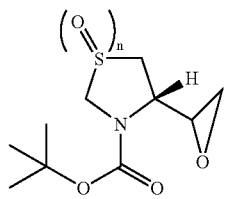

A. Preparation of 4-(2-diazo-acetyl)-thiazolidine-3-carboxylic acid tert-butyl ester

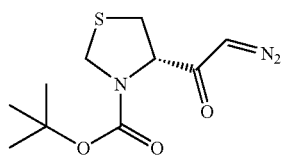

Diazomethane preparation: To a cold mixture of KOH solution (15 g in 37 mL water) and Et$_2$O (125 mL) at 0° C.

was slowly added MNNG (1-methyl-3-nitro-1-nitrosoguanidine) (11.7 g, 79.5 mmol) in portions. Gas was evolved. This bi-phasic mixture was kept at 0° C. until no more gas evolved. The yellow ether layer was decanted into a dry flask and kept at 0° C. ready to use in the next reaction.

To a solution of Boc-D-thiozolidine-4-carboxylic acid (5.0 g, 21.4 mmol) and triethylamine (3.0 mL, 21.4 mmol) in THF (50 mL) at −10° C. (ice in acetone) was added dropwise isobutylchloroformate (2.76 mL, 21.4 mmol). The reaction was stirred at −10° C. for 30 min. The resulting white precipitate was filtered and the filtrate was maintained at −10° C. To this solution was added the solution of diazomethane in ether prepared above. The reaction was stirred at −10° C. for 1 h, then warmed to room temperature. Ethyl acetate was added and the solution was washed with $H_2O$, saturated $NaHCO_3$ solution, and brine, then dried over $MgSO_4$. Evaporation of the solvent gave a yellow oil. Purification was performed by flash chromatography on silica gel, loading with $CH_2Cl_2$ and eluting with 25% ethyl acetate in hexane. Pure fractions were combined and evaporated to give the title compound (4.5 g, 82%) as a pale yellow oil.

MS (ES+) m/z 280 [M+Na]$^+$ $^1$H NMR (400 MHz, CDCl$_3$): δ 1.48 (s, 9H); 3.3 (m, 1H); 4.4 (m, 1H); 4.68 (m, 2H); 5.53 (s, 1H).

B. Preparation of 4-(2-chloro-acetyl)-thiazolidine-3-carboxylic acid tert-butyl ester

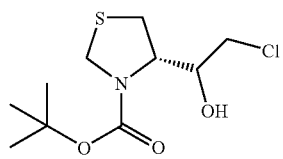

To a solution of the Part A compound above (4.5 g, 17.5 mmol) in $CH_2Cl_2$ (150 mL) at −10° C., was added 4N HCl in dioxane (20 mL) dropwise. Gas was evolved and the reaction was stirred at −10° C. for 1 h., then evaporated to dryness to give the title compound (4.5 g, 97%) as a yellow oil.

$^1$H NMR (500 MHz, CDCl$_3$): δ 1.49 (s, 9H); 3.23 (m, 2H); 3.71 (s, 2H); 4.34–4.91 (broad, 3H).

C. Preparation of 4-(2-chloro-1-hydroxy-ethyl)-thiazolidine-3-carboxylic acid tert-butyl ester

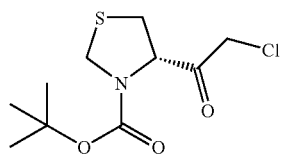

To a solution of the Part B chloroketone (4.5 g, 16.9 mmol) in MeOH/THF (1:1, 20 mL) at 0° C. was added NaBH$_4$ (642 mg, 16.9 mmol). The reaction was stirred at 0° C. for 1 h. Acetic acid was added dropwise until pH=5 to quench the reaction. The organic solvents were evaporated to dryness. The resulting residue was dissolved in ethyl acetate and the organic layer was washed with saturated NaHCO$_3$ solution and brine, then dried over MgSO$_4$. Evaporation of the solvent gave the title compound (4.2 g, 93%%) as a crude oil.

D. Preparation of 4-oxiranyl-thiazolidine-3-carboxylic acid tert-butyl esters

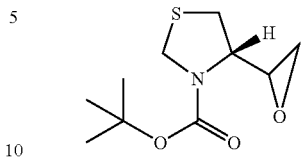

The Part C compound (4.2 g, 15.7 mmol) was dissolved in isopropanol (10 mL). The solution was cooled to 0° C. and 4N aqueous KOH solution (10 mL) was added. The reaction mixture was stirred for 30 min at room temperature. Ethyl acetate was added and the organic layer was washed with saturated NaHCO$_3$ solution and brine, then dried over MgSO$_4$. Purification of the mixture of the diastereoisomers was performed by flash chromatography on silica gel, loading with CH$_2$Cl$_2$ and eluting with 8% ethyl acetate in hexane to give the (S,R) diastereoisomer (710 mg) as an oil, and the (S,S) diastereoisomer (1.9 g) as an oil.

(S,R) Diastereoisomer:

$^1$H NMR (400 MHz, CDCl$_3$): δ 1.48 (s, 9H); 2.7 (m, 1H); 2.77 (t, 1H, J=4.3 Hz); 2.9 (q, 1H); 3.15 (m, 2H); 4.22 (d, 1H, J=9.12 Hz); 4.68 (broad s, 2H).

$^{13}$C NMR (400 MHz, CD$_3$OD): δ 28.19; 31.87; 44.86; 48.79; 52.19; 58.64; 80.90; 153.49.

(S,S) Diastereoisomer:

$^1$H NMR (400 MHz, CDCl$_3$): δ 1.48 (s, 9H); 2.9 (m, 2H); 3.13 (m, 3H); 3.85 (m, 1H); 4.35 (m, 1H); 4.57 (broad, 1H);

$^{13}$C NMR (400 MHz, CD$_3$OD): δ 28.27; 33.01; 34.37; 47.91; 48.98; 51.89; 80.81; 153.34.

E. Preparation of 4-Oxiranyl-1,1-dioxo-1λ$^6$-thiazolidine-3-carboxylic acid tert-butyl ester

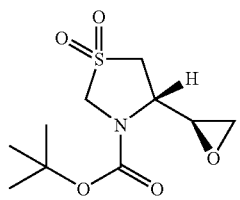

To a solution of the Part B chloroketone (2 g, 7.5 mmol) in anhydrous THF (20 mL) at −78° C. was added dropwise L-Selectride (12.8 mL, 1N in THF, 12.8 mmol). The reaction was stirred at −78° C. for 30 min. Acetic acid (1.02 g, 17.04 mmol), LiOH (1.18 g, 28 mmol) and H$_2$O$_2$ (9.6 mL, 42.4 mmol) were added dropwise until pH=5. The mixture was slowly warmed to room temperature. The resulting mixture was dissolved in ethyl acetate and the organic layer was washed with saturated NaHCO$_3$ solution and brine, then dried over MgSO$_4$. Evaporation of the solvent gave 2.1 g of a colorless oil. The residue was dissolved in isopropanol and 4N aqueous KOH (10 mL) was added. The mixture was stirred for 1 h at room temperature. Ethyl acetate was added and the organic layer was washed with saturated NaHCO$_3$ solution and brine, then dried over MgSO$_4$. Evaporation of the solvent gave a crude product which was purified by flash chromatography on silica gel, loading with CH$_2$Cl$_2$ and eluting with 45% ethyl acetate in hexane. Pure fractions were combined and evaporated to give the title compound (510 mg, 26%) as a white solid.

$^1$H NMR (400 MHz, CDCl$_3$): δ 1.49 (s, 9H); 2.74 (m, 1H); 2.88 (t, 1H, J=3.8 Hz); 3.18–3.25 (m, 2H); 3.46 (q, 1H, J=10.7 and 9.12 Hz); 4.07 (d, 1H, J=12.4 Hz); 4.78 (broad s, 1H); 5.05 (broad s, 1H)

$^{13}$C NMR (400 MHz, CD$_3$OD): δ 27.99; 45.39; 50.13; 52.51; 63.18; 82.87; 153.14.

Preparation 3

2-(1,1-Dimethyl-2-naphthalen-2-yl-ethylamino)-1-thiazolidin-4-yl-ethanol

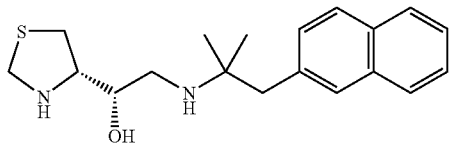

A. Preparation of 4-[2-(1,1-Dimethyl-2-naphthalen-2-yl-ethylamino)-1-hydroxy-ethyl]-thiazolidine-3-carboxylic acid tert-butyl ester

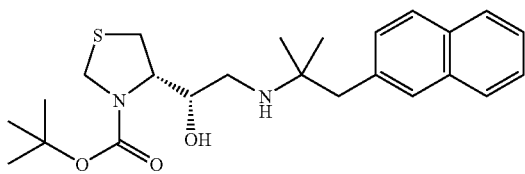

A mixture of the Preparation 2 Part D (S,R) diastereoisomer (100 mg, 0.43 mmol) and 1,1-dimethyl-2-naphthalen-2-yl-ethylamine (86 mg, 0.43 mmol) were dissolved in CH$_2$Cl$_2$, then the solvent was evaporated to make a homogenous mixture, which was heated at 90° C. overnight, then cooled to room temperature. Purification was performed by flash chromatography on silica gel, loading with CH$_2$Cl$_2$ and eluting with 2% MeOH in CH$_2$Cl$_2$ containing 0.2% NH$_4$OH. Pure fractions were combined and evaporated to give the title compound (150 mg, 81%) as a colorless oil.

$^1$H NMR (400 MHz, CDCl$_3$): δ 1.31 (s, 3H); 1.33 (s, 3H);2.16 (s, 3H); 2.75 (m, 1H); 2.99 (m, 1H); 3.13 (s, 2H) 3.26 (m, 2H); 3.4 (m, 1H); 3.65 (s, 2H); 3.75 (m, 1H); 4.02 (d, 1H, J=10.2 Hz); 4.20 (d, 1H, J=10.2 Hz); 6.76 (d, 1H, J=4.8 Hz); 7.11 (d, 1H, J=4.8 Hz); 7.32 (d, 1H, J=8.6 Hz); 7.42–7.52 (m, 2H); 7.9 (s, 1H); 7.77–7.85 (m, 3H).

MS (ES+) m/z 431.3 [M+H]$^+$.

HPLC retention time=6.33 min (Method B).

B. Preparation of 2-(1,1-Dimethyl-2-naphthalen-2-yl-ethylamino)-1-thiazolidin-4-yl-ethanol

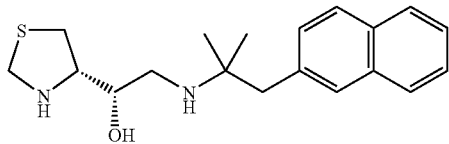

To a solution of the Part A compound (150 mg, 0.35 mmol) in CH$_2$Cl$_2$ (3 mL) was added 4N HCl in dioxane (4 mL). The reaction was stirred at room temperature for 2.5 h. The reaction mixture was evaporated to dryness. The resulting oil was dissolved in ethyl acetate and the solution was washed with saturated NaHCO$_3$ and brine, then dried over MgSO$_4$. Evaporation gave the title compound (106 mg, 92%) as a colorless oil.

MS (ES+) m/z 331.2 [M+H]$^+$.

HPLC retention time=3.10 min (Method A).

Preparation 4

2-(1,1-Dimethyl-2-naphthalen-2-yl-ethylamino)-1-thiazolidin-4-yl-ethanol

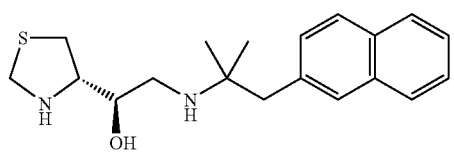

A. Preparation of 4-[2-(1,1-dimethyl-2-naphthalen-2-yl-ethylamino)-1-hydroxy-ethyl]-1,1-dioxo-1λ$^6$-thiazolidine-3-carboxylic acid tert-butyl ester

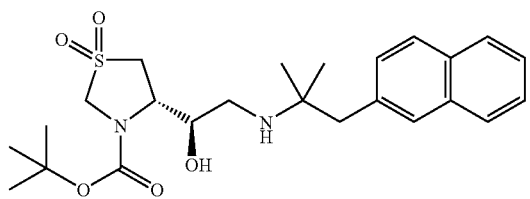

A mixture of the Preparation 2 Part E compound (220 mg, 0.84 mmol) and 1,1-dimethyl-2-naphthalen-2-yl-ethylamine (167 mg, 0.84 mmol) were mixed, heated at 90° C. overnight, then cooled to room temperature. Purification was performed by flash chromatography on silica gel, loading with CH$_2$Cl$_2$ and eluting with 5% MeOH in CH$_2$Cl$_2$. Pure fractions were combined and evaporated to give the title compound (220 mg, 57%) as a white foam.

MS (ES+) m/z 463.4 [M+H]$^+$.

HPLC retention time=5.96 min (Method B).

B. Preparation of 4-[2-(1,1-dimethyl-2-naphthalen-2-yl-ethylamino)-1-hydroxy-ethyl]-thiazolidine-3-carboxylic acid tert-butyl ester

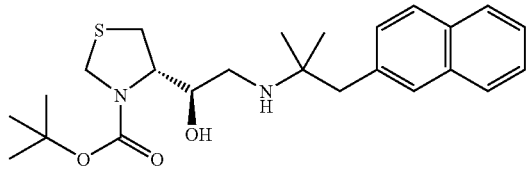

To a solution of the Part A compound (30 mg, 0.06 mmol) in THF was added lithium aluminium hydride solution (0.06 mL, 1M in THF, 0.06 mmol). The mixture was stirred at room temperature overnight. Sodium potassium tartrate solution was added and the mixture was stirred at room temperature for 5 h. Ethyl acetate was added and the organic layer was washed with brine and dried over MgSO₄. Evaporation to dryness gave the title compound as an oil.
MS (ES+) m/z 431.3 [M+H]⁺.
HPLC retention time=6.32 min (Method B).

C. Preparation of 2-(1,1-dimethyl-2-naphthalen-2-yl-ethylamino)-1-thiazolidin-4-yl-ethanol

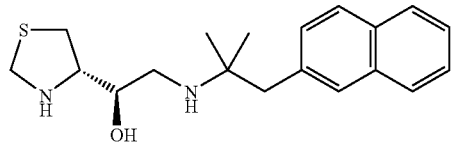

According to the experimental procedure for the preparation of the Preparation 3 Part B compound, hydrolysis of the BOC protecting group of the Part B compound gave the title compound (106 mg, 92%) as a colorless oil.
MS (ES+) m/z 331.4 [M+H]⁺.
HPLC retention time=2.24 min (Method C).

Following one of the procedures described in Preparations 1–4 and by using the appropriated amines and oxiranyl thiazolidines, the following intermediates were synthesized.

Intermediate 1

4-{1-Hydroxy-2-[2-(4-methoxy-phenyl)-1,1-dimethyl-ethylamino]-ethyl}-thiazolidine-3-carboxylic acid tert-butyl ester

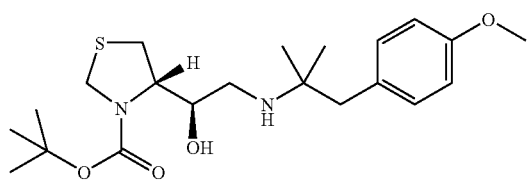

Purified by flash chromatography on silica gel, loading with CH₂Cl₂ and eluting with 3% MeOH in CH₂Cl₂ containing 0.2% NH₄OH, and obtained as a colorless oil.
MS (ES+) m/z 411.4 [M+H]⁺.
HPLC retention time=2.59 min (Method A).

Intermediate 2

4-{1-Hydroxy-2-[2-(4-methoxy-phenyl)-1,1-dimethyl-ethylamino]-ethyl}-thiazolidine-3-carboxylic acid tert-butyl ester

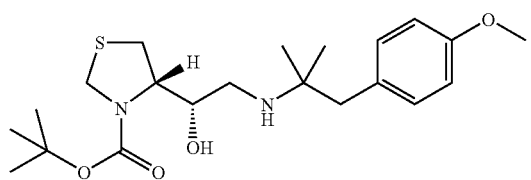

Purified by flash chromatography on silica gel, loading with CH₂Cl₂ and eluting with 3% MeOH in CH₂Cl₂ containing 0.2% NH₄OH, and obtained as a colorless oil.
MS (ES+) m/z 411.3 [M+H]⁺.
HPLC retention time=5.50 min (Method B).

Intermediate 3

4-[2-(2-Benzothiazol-2-yl-1,1-dimethyl-ethylamino)-1-hydroxy-ethyl]-thiazolidine-3-carboxylic acid tert-butyl ester

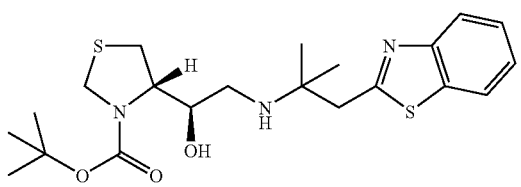

Purified by flash chromatography on silica gel, loading with CH₂Cl₂ and eluting with 5% MeOH in CH₂Cl₂ containing 0.2% NH₄OH, and obtained as a colorless oil.
MS (ES+) m/z 438.4 [M+H]⁺.

Intermediate 4

4-[2-(2-Benzothiazol-2-yl-1,1-dimethyl-ethylamino)-1-hydroxy-ethyl]-thiazolidine-3-carboxylic acid tert-butyl ester

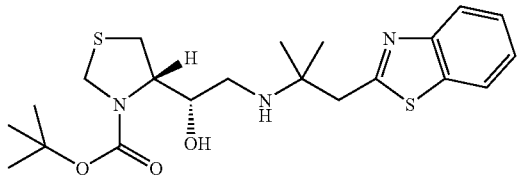

Purified by flash chromatography on silica gel, loading with CH₂Cl₂ and eluting with 3% MeOH in CH₂Cl₂ and obtained as a colorless oil.
MS (ES+) m/z 438.2 [M+H]⁺.
HPLC retention time=4.96 min (Method A).

Intermediate 5

2-[2-(4-Methoxy-phenyl)-1,1-dimethyl-ethylamino]-1-thiazolidin-4-yl-ethanol

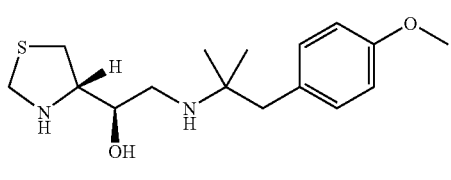

MS (ES+) m/z 311.2 [M+H]⁺.

Intermediate 6

2-[2-(4-Methoxy-phenyl)-1,1-dimethyl-ethylamino]-1-thiazolidin-4-yl-ethanol

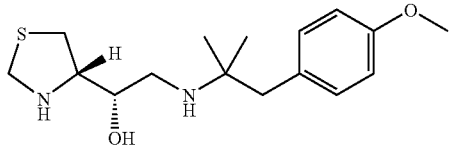

MS (ES+) m/z 311.2 [M+H]$^+$.
HPLC retention time=1.06 min (Method A).

Intermediate 7

2-(2-Benzothiazol-2-yl-1,1-dimethyl-ethylamino)-1-thiazolidin-4-yl-ethanol

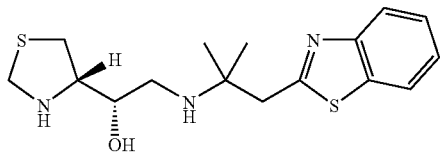

MS (ES+) m/z 338.1 [M+H]$^+$.
HPLC retention time=1.92 min (Method A).

Intermediate 8

2-(2-Benzothiazol-2-yl-1,1-dimethyl-ethylamino)-1-thiazolidin-4-yl-ethanol

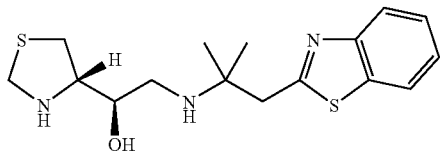

MS (ES+) m/z 338.1 [M+H]$^+$.

Intermediate 9

2-(1,1-Dimethyl-2-naphthalen-2-yl-ethylamino)-1-(1,1-dioxo-1$\lambda^6$-thiazolidin-4-yl)-ethanol

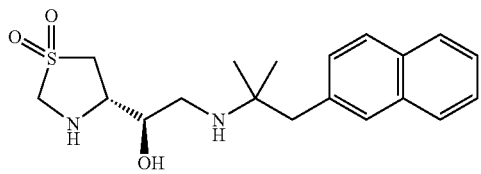

MS (ES+) m/z 363.3 [M+H]$^+$
HPLC retention time=2.03 min (Method A).

Utilizing the aforementioned procedures and intermediates, the following exemplary compounds were prepared.

EXAMPLE 1

3-{4-[2-(1,1-Dimethyl-2-naphthalen-2-yl-ethylamino)-1-hydroxy-ethyl]-thiazolidin-3-ylmethyl}-benzonitrile

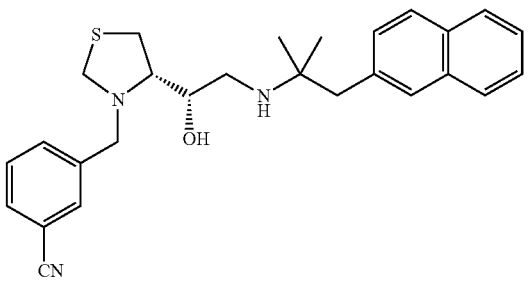

The Preparation 3 compound (10 mmol) and 3-cyanobenzaldehyde (10 mmol) were mixed, in 1,2-dichloroethane (35 mL) and then treated with sodium triacetoxyborohydride (14 mmol). The mixture was stirred at room temperature under a N$_2$ atmosphere for 1.5 h. The reaction mixture was quenched by adding aqueous saturated NaHCO$_3$ and the product was extracted with EtOAc. The organic layer was dried over MgSO$_4$ and the solvent was evaporated to give the crude product, which was purified by flash chromatography on silica gel, loading with CH$_2$Cl$_2$ and eluting with 2% MeOH in CH$_2$Cl$_2$ containing 0.2% NH$_4$OH, to provide the title compound.

$^1$H NMR (400 MHz, CDCl$_3$): δ 1.10 (s, 3H); 1.11 (s, 3H); 2.54 (q, 1H, J=11.8 and 6.96 Hz); 2.83 (q, 2H); 2.92 (q, 1H); 3.04 (q, 1H, J=10.76 Hz); 3.15 (t, 1H); 3.26 (q, 1H, J=8.6 and 2.16 Hz); 3.35 (m, 1H); 3.42 (d, 1H, J=13.7 Hz); 3.57 (d, 1H, J=13.7 Hz); 3.82 (d, 1H, J=10.2 Hz); 3.98 (d, 1H, J=10.2 Hz) 7.3 (m, 2H); 7.35–7.5 (m, 4H); 7.52 (s, 1H); 7.59 (s, 1H); 7.71–7.8 (m, 3H).

$^{13}$C NMR (400 MHz, CD$_3$OD): δ 26.72; 26.99; 31.66; 44.77; 48.25; 53.38; 58.04; 59.14; 69.25; 72.37; 112.47; 118.55; 125.37; 125.91; 127.38; 127.46; 128.75; 129.01; 129.07; 130.94; 132.06; 132.94; 133.17; 135.42; 140.18.

MS (ES+) m/z 446.3 [M+H]$^+$.

HPLC retention time=6.02 min (Method B).

EXAMPLE 2

3-{4-[2-(1,1-Dimethyl-2-naphthalen-2-yl-ethylamino)-1-hydroxy-ethyl]-thiazolidin-3-ylmethyl}-benzonitrile

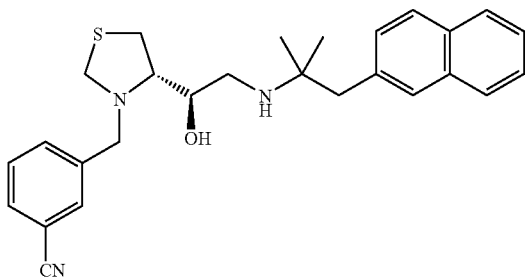

The Preparation 4 compound (10 mmol) and 3-cyanobenzaldehyde (10 mmol) were mixed in 1,2-dichloroethane (35 mL) and then treated with sodium triacetoxyborohydride (14 mmol). The mixture was stirred at room temperature under a $N_2$ atmosphere for 1.5 h. The reaction mixture was quenched by adding aqueous saturated $NaHCO_3$ and the product was extracted with EtOAc. The organic layer was dried over $MgSO_4$ and the solvent was evaporated to give the crude product, which was purified by flash chromatography on silica gel, loading with $CH_2Cl_2$ and eluting with 2% MeOH in $CH_2Cl_2$ containing 0.2% $NH_4OH$, to provide the title compound.

$^1$H NMR (400 MHz, $CDCl_3$): δ 1.101 (s, 3H); 1.103 (s, 3H); 2.63 (q, 1H, J=11.6 and 6.2 Hz); 2.85 (m, 4H); 3.04 (q, 1H, J=7 Hz); 3.5 (m, 1H); 3.56 (d, 1H, J=13.4 Hz); 3.74 (q, 1H, J=14 Hz); 3.85 (d, 1H, J=10.2 Hz); 4.07 (d, 1H, J=10.2 Hz); 7.3 (q, 1H); 7.4–7.5 (m, 3H); 7.57 (m, 2H); 7.63 (s, 2H); 7.74–7.8 (m, 3H).

$^{13}$C NMR (400 MHz, $CD_3OD$): δ 26.81; 26.97; 31.56; 44.77; 47.49; 53.39; 57.66; 69.84; 72.06; 112.68; 118.5; 125.33; 125.87; 127.27; 127.51; 128.80; 129.17; 129.36; 131.29; 132.04; 132.34; 133.28; 135.80; 139.81.

MS (ES+) m/z 446.2 [M+H]$^+$.

HPLC retention time=5.94 min (Method B).

EXAMPLE 3

3-(4-{1-Hydroxy-2-[2-(4-methoxy-phenyl)-1,1-dimethyl-ethylamino]-ethyl}-thiazolidin-3-ylmethyl)-benzonitrile

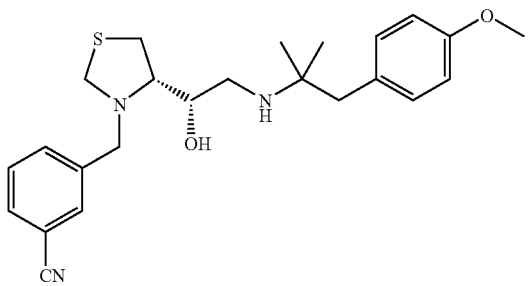

A mixture of the Intermediate 6 compound (50 mg, 0.161 mmol), of alpha-bromometatolunitrile (31.6 mg, 1.16 mmol) and of $K_2CO_3$ (22.3 mg, 0.161 mmol) and DMF (1 mL) was stirred at 50° C. for 1 h, then at room temperature overnight. Water (5 mL) was added and the solution was extracted with AcOEt (4×5 mL). The organic phases were combined, dried over $MgSO_4$, and evaporated to dryness to yield 76 mg of a colorless oil. Purification by flash chromatography gave the title compound (36 mg, 53%) as an oil.

The free amine prepared above was dissolved in small amount of $CH_2Cl_2$. A solution of HCl in ether (1 mL, 1M, 1 mmol) was added and the mixture stirred for 30 min. The volatiles were evaporated and the residue triturated with petroleum ether/methanol to provide the hydrochloride salt of the title compound as a white solid.

mp=158–163° C.

$^1$H NMR (400 MHz, $CD_3OD$): δ 1.32 (s, 6H); 2.3 (m, 2H); 3.2–3.45 (m, 9H); 3.78 (s, 3H); 4.09 (s, 1H); 6.92 (d, 2H, J=8.4 Hz); 7.2 (d, 2H, J=8.4 Hz); 7.58 (m, 1H); 7.71 (m, 2H); 7.84 (s, 1H).

MS (ES+) m/z 426.2 [M+H]$^+$.

HPLC retention time=4.57 min (Method A).

According to the methods described in Examples 1–3 above and by using the appropriate starting materials, the following exemplary compounds were prepared.

EXAMPLE 4

2-(1,1-Dimethyl-2-naphthalen-2-yl-ethylamino)-1-{3-[4-(furan-2-ylmethylsulfanyl)-3-nitro-benzyl]-thiazolidin-4-yl}-ethanol

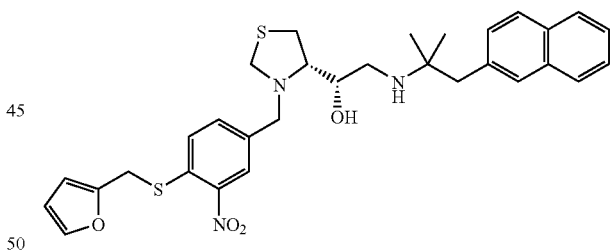

$^1$H NMR (500 MHz, $CDCl_3$): δ 1.11 (s, 3H); 1.12 (s, 3H); 1.25 (broad s, 2H); 2.2 (broad s, 1H); 2.67 (m, 1H); 2.86 (m, 4H) 3.05 (m, 1H); 3.51 (m, 1H); 3.58 (d, 1H, J=10 Hz); 3.75 (d, 1H, J=10 Hz); 3.87 (d, 1H, J=10 Hz); 4.09 (d, 1H, J=10 Hz); 6.31 (m, 2H); 7.32 (q, 1H); 7.37 (d, 1H); 7.44 (m, 3H); 7.52 (q, 1H); 7.63 (s, 1H); 7.75–7.82 (m, 3H); 8.16 (d, 1H, J=5 Hz).

mp=80–85° C.

MS (ES+) m/z 578.3 [M+H]$^+$.

HPLC retention time=6.93 min (Method B).

EXAMPLE 5

2-(1,1-Dimethyl-2-naphthalen-2-yl-ethylamino)-1-[3-(3-methyl-thiophen-2-ylmethyl)-thiazolidin-4-yl]-ethanol

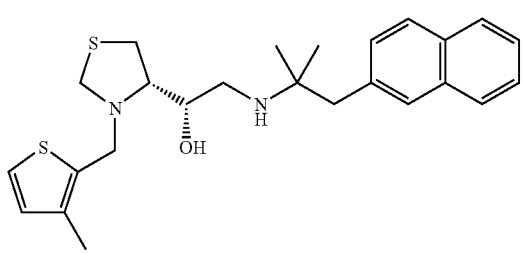

¹H NMR (400 MHz, CDCl₃): δ 1.31 (s, 3H); 1.33 (s, 3H); 2.16 (s, 3H); 2.75 (m, 1H); 2.99 (m, 1H); 3.13 (s, 2H) 3.26 (m, 2H); 3.4 (m, 1H); 3.65 (s, 2H); 3.75 (m, 1H); 4.02 (d, 1H, J=10.2 Hz); 4.20 (d, 1H, J=10.2 Hz); 6.76 (d, 1H, J=4.8 Hz); 7.11 (d, 1H, J=4.8 Hz); 7.32 (d, 1H, J=8.6 Hz); 7.42–7.52 (m, 2H); 7.9 (s, 1H); 7.77–7.85 (m, 3H);
MS (ES+) m/z 441.3 [M+H]⁺.
HPLC retention time=6.77 min (Method B).

EXAMPLE 6

1-[3-(2-Chloro-6-methoxy-quinolin-3-ylmethyl)-thiazolidin-4-yl]-2-(1,1-dimethyl-2-naphthalen-2-yl-ethylamino)-ethanol

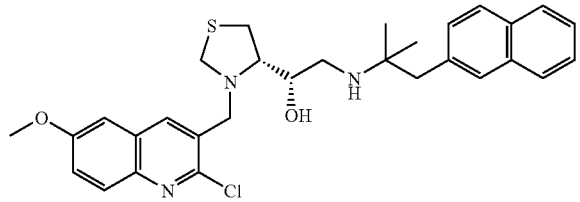

¹H NMR (400 MHz, CDCl₃): δ 1.047 (s, 3H); 1.05 (s, 3H); 2.58 (q, 1H, J=7.52 Hz); 2.77 (s, 2H); 2.98 (q, 1H); 3.15 (m, 1H, J=4.28 Hz); 3.3–3.4 (m, 3H); 3.69 (d, 1H, J=14.5 Hz); 3.8 (d, 1H, J=14.5 Hz); 3.88 (s, 3H); 3.99 (q, 1H, J=11.3 Hz); 7.02 (d, 1H, J=2.68 Hz); 7.24 (q, 1H); 7.36 (q, 1H, J=9.16 and 2.68 Hz); 7.38–7.46 (m, 2H); 7.54 (s, 1H); 7.68 (d, 1H, J=8.08 Hz); 7.73 (q, 2H); 7.9 (d, 1H, J=9.12 Hz); 7.99 (s, 1H).
MS (ES+) m/z 536.3 [M+H]⁺.
HPLC retention time=6.76 min (Method B).

EXAMPLE 7

2-{4-[2-(1,1-Dimethyl-2-naphthalen-2-yl-ethylamino)-1-hydroxy-ethyl]-thiazolidin-3-ylmethyl}-6-fluoro-phenol

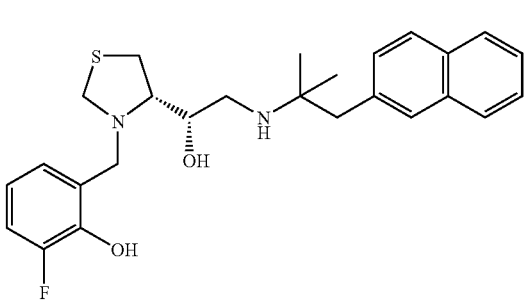

¹H NMR (400 MHz, CDCl₃): δ 1.25 (s, 3H); 1.28 (s, 3H); 2.68 (q, 1H, J=9.16 and 11.8 Hz); 3.01 (s, 2H); 3.07 (q, 1H, J=7 and 10.8 Hz); 3.12 (q, 1H); 3.21 (q, 1H); 3.3 (t, 1H); 3.69 (t, 1H); 3.78 (s, 2H); 3.94 (d, 1H, J=10.8 Hz); 3.98 (d, 1H, J=10.8 Hz); 6.77 (m, 2H); 7.02 (m, 1H); 7.27 (m, 1H); 7.4–7.5 (m, 2H); 7.63 (s, 1H); 7.7–7.82 (m, 3H).
MS (ES+) m/z 455.3 [M+H]⁺.
HPLC retention time=6.18 min (Method B).

EXAMPLE 8

1-[3-(1-Benzenesulfonyl-1H-pyrrol-2-ylmethyl)-thiazolidin-4-yl]-2-(1,1-dimethyl-2-naphthalen-2-yl-ethylamino)-ethanol

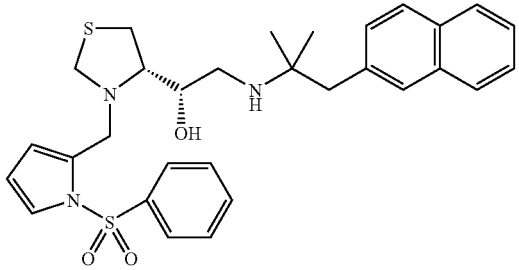

¹H NMR (400 MHz, CD₃OD): δ 1.19 (s, 3H); 1.22 (s, 3H); 2.72 (q, 1H, J=8.6 and 11.8 Hz); 3.0 (m, 3H); 3.2 (q, 1H); 3.3–3.5 (m, 3H); 3.7 (s, 2H); 3.92 (d, 1H, J=10.2 Hz); 3.98 (d, 1H, J=10.2 Hz); 6.26 (m, 2H); 7.32 (m, 1H); 7.35 (m, 1H); 7.4–7.5 (m, 2H); 7.55–7.6 (m, 2H); 7.65 (d, 1H); 7.7 (s, 1H); 7.78–7.9 (m, 5H).
MS (ES+) m/z 550.3 [M+H]⁺.
HPLC retention time=6.78 min (Method B).

Example 9

2-{4-[2-(1,1-Dimethyl-2-naphthalen-2-yl-ethylamino)-1-hydroxy-ethyl]-thiazolidin-3-ylmethyl}-6-nitro-phenol

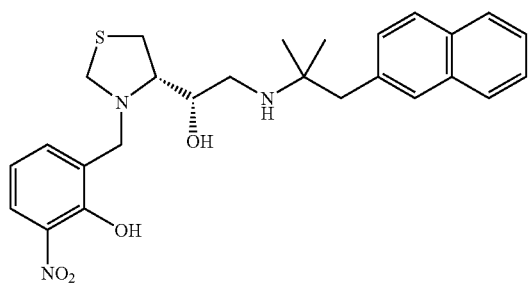

$^1$H NMR (500 MHz, CDCl$_3$): δ 1.18 (s, 3H); 1.19 (s, 3H); 2.7 (q, 1H); 2.93 (s, 2H); 3.2 (M, 1H); 3.23 (q, 1H); 3.29 (t, 1H); 3.54 (m, 1H); 3.63 (d, 1H); 3.64 (d, 1H); 3.87 (d, 1H); 3.97 (d, 1H); 6.84 (t, 1H); 7.27 (m, 1H); 7.4–7.5 (m, 3H); 7.59 (s, 1H); 7.75 (m, 3H); 7.98 (d, 1H).
MS (ES+) m/z 482.3 [M+H]$^+$.
HPLC retention time=6.38 min (Method B).

EXAMPLE 10

1-[3-(2-Chloro-quinolin-3-ylmethyl)-thiazolidin-4-yl]-2-[2-(4-methoxy-phenyl)-1,1-dimethyl-ethylamino]-ethanol

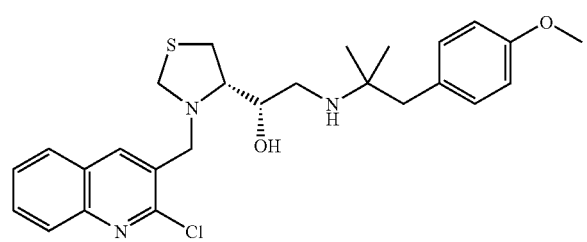

$^1$H NMR (400 MHz, CDCl$_3$): δ 1.01 (s, 3H); 1.03 (s, 3H); 1.26 (broad s, 2H); 2.55 (q, 1H); 2.59 (s, 2H); 2.8 (broad s, 2H); 3 (q, 1H); 3.15 (m, 1H); 3.33 (m, 2H); 3.42 (m, 1H); 3.74 (m, 4H); 3.85 (d, 1H, J=14.5); 3.99 (q, 2H, J=8.6) 6.75 (d, 2H, J=8.6 Hz); 7.0 (d, 2H, J=8.6 Hz); 7.58 (t, 1H, J=7 Hz); 7.74 (sextuplet, 1H, J=7 Hz and 1.6 Hz); 7.80 (d, 1H, J=8.08 Hz); 8.03 (t, 1H, J=8.6 Hz); 8.13 (s, 1H).
MS (ES+) m/z 486.3 [M+H]$^+$.
HPLC retention time=5.9 min (Method B).

EXAMPLE 11

1-[3-(2-Chloro-quinolin-3-ylmethyl)-thiazolidin-4-yl]-2-(1,1-dimethyl-2-naphthalen-2-yl-ethylamino)-ethanol

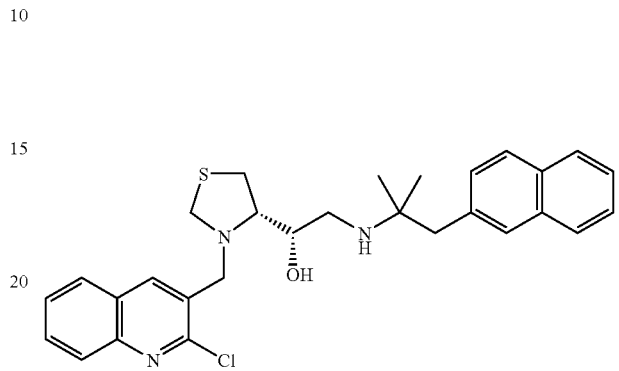

$^1$H NMR (400 MHz, CDCl$_3$): δ 1.14 (s, 6H); 1.23 (broad s, 2H); 2.62 (q, 1H, J=11.8 and 8.04 Hz); 2.88 (s, 2H); 3.13 (m, 2H); 3.34 (m, 2H); 3.45 (m, 1H); 3.67 (d, 1H, J=14 Hz); 3.81 (d, 1H, J=14 Hz); 3.95 (d, 1H, J=10.2 Hz); 4.06 (d, 1H, J=10.2 Hz); 7.24 (m, 1H); 7.42 (m, 2H); 7.57 (m, 2H); 7.68–7.8 (m, 5H); 8.02 (d, 1H, J=8.6 Hz); 8.07 (s, 1H).
MS (ES+) m/z 506.2 [M+H]$^+$.
HPLC retention time=6.63 min (Method B).

EXAMPLE 12

4-(4-{1-Hydroxy-2-[2-(4-methoxy-phenyl)-1,1-dimethyl-ethylamino]-ethyl}-thiazolidin-3-ylmethyl)-benzonitrile

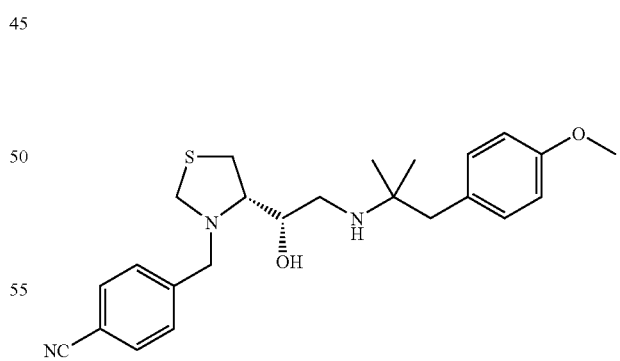

$^1$H NMR (400 MHz, CDCl$_3$): δ 1.31 (s, 3H); 1.34 (s, 3H); 2.75 (broad s, 1H); 2.91 (m, 2H); 3.13 (m, 1H); 3.3 (m, 1H); 3.55 (m, 1H); 3.79 (s, 3H); 3.94 (m, 3H); 4.068–4.095 (m, 3H); 6.87 (d, 2H, J=8.6 Hz); 7.09 (d, 2H, J=8.6 Hz); 7.46 (d, 2H, J=8.08 Hz); 7.67 (d, 2H, J=8.08 Hz).
MS (ES+) m/z 426.2 [M+H]$^+$.
HPLC retention time=4.73 min (Method A).

EXAMPLE 13

3-{4-[2-(2-Benzothiazol-2-yl-1,1-dimethyl-ethylamino)-1-hydroxy-ethyl]-thiazolidin-3-ylmethyl}-benzonitrile $^1$H NMR (400 MHz, CDCl$_3$): δ 1.51 (s, 3H); 1.58 (s, 3H); 2.8 (m, 1H); 3.1–3.3 (m, 2H); 3.3–3.5 (m, 4H); 3.63 (d, 1H); 3.7 (d, 1H); 3.9 (d, 1H, J=10.5 Hz); 4 (m, 1H); 4.03 (d, 1H, J=10.5 Hz); 7.4–7.53 (m, 5H); 7.64 (s, 1H); 7.86 (d, 1H, J=7.5 Hz); 7.97 (d, 1H, J=8.04 Hz).

MS (ES+) m/z 453.2 [M+H]$^+$.

HPLC retention time=4.76 min (Method B).

It should be understood that while this invention has been described herein in terms of specific embodiments set forth in detail, such embodiments are presented by way of illustration of the general principles of the invention, and the invention is not necessarily limited thereto. Certain modifications and variations in any given material, process step or chemical formula will be readily apparent to those skilled in the art without departing from the true spirit and scope of the present invention, and all such modifications and variations should be considered within the scope of the claims that follow.

What is claimed is:

1. A compound of the formula I wherein

Ar$^1$ is a substituted or unsubstituted aryl or substituted or unsubstituted heteroaryl;

X is a linking group selected from alkylene, CO, alkyleneCO, OCO, alkyleneOCO, SO$_2$ and alkyleneSO$_2$;

J is a linking group selected from S, SO and SO$_2$;

R$^1$ and R$^2$ are each independently substituted or unsubstituted C$_1$–C$_4$ alkyl, or R$^1$ can be cyclized with R$^2$ to form (—CH$_2$—)$_m$ where m is an integer from 2 to 5;

R$^3$ is hydrogen (H) or alkyl;

Q is Ar$^1$ or G;

G is z is 1 or 2;

R$^4$, R$^5$ and R$^6$ are each independently selected from hydrogen (H), halo, haloalkyl, alkyl, alkoxy, haloalkoxy, hydroxy, cyano, nitro, amino, alkylamino and alkylthio;

R$^7$ and R$^8$ are each independently selected from hydrogen (H), alkyl, aryl and heteroaryl;

including all prodrug esters, pharmaceutically acceptable salts or stereoisomers thereof.

2. The compound as defined in claim 1 wherein

X is alkylene;

J is sulfur (S);

R$^1$ and R$^2$ are methyl, or R$^1$ is cyclized with R$^2$ to form a cyclopropyl ring;

R$^3$ is hydrogen;

z is 2;

Q is substituted or unsubstituted phenyl or naphthyl, or G;

R$^4$, R$^5$ and R$^6$ are hydrogen; and

R$^7$ and R$^8$ are hydrogen.

3. The compound as defined in claim 1 wherein the compound is selected from:

4. The compound as defined in claim 1 wherein the compound is selected from:

-continued

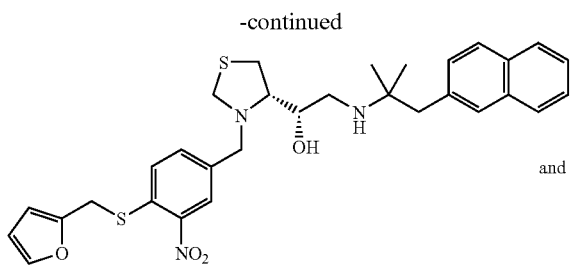

and

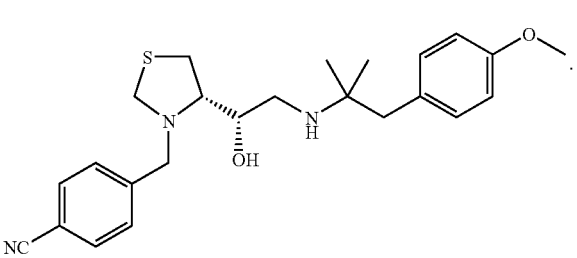

5. A pharmaceutical composition comprising a compound as defined in claim 1 and a pharmaceutically acceptable carrier therefor.

6. The pharmaceutical composition of claim 5 further comprising at least one additional therapeutic agent selected from other compounds of formula I, anti-osteoporosis agents, cholesterol/lipid lowering agents, growth promoting agents, progesterone receptor agonists, modulators of bone resorption, selective estrogen receptor modulators, selective androgen receptor modulators, vitamin D, vitamin D analogues, elemental calcium, PTH, osteoprotegrin, tibolone and isoflavinoids.

7. A pharmaceutical composition capable of modulating the calcium sensing receptor comprising a compound of formula I

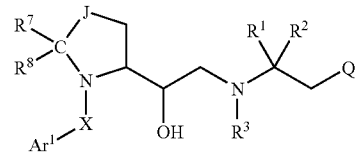

wherein
$Ar^1$ is a substituted or unsubstituted aryl or substituted or unsubstituted heteroaryl;
X is a linking group selected from alkylene, CO, alkyleneCO, OCO, alkyleneOCO, $SO_2$ and alkylene$SO_2$;
J is a linking group selected from S, SO and $SO_2$;
$R^1$ and $R^2$ are each independently substituted or unsubstituted $C_1$–$C_4$ alkyl, or $R^1$ can be cyclized with $R^2$ to form (—$CH_2$—)$_m$ where m is an integer from 2 to 5;
$R^3$ is hydrogen (H) or alkyl;
Q is $Ar^1$ or G;
G is

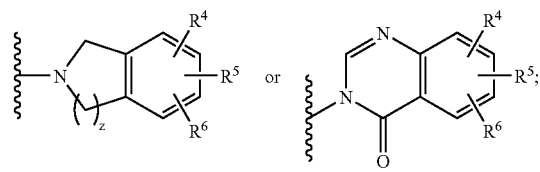

z is 1 or 2;
$R^4$, $R^5$ and $R^6$ are each independently selected from hydrogen (H), halo, haloalkyl, alkyl, alkoxy, haloalkoxy, hydroxy, cyano, nitro, amino, alkylamino and alkylthio;
$R^7$ and $R^8$ are each independently selected from hydrogen (H), alkyl, aryl and heteroaryl;
including all prodrug esters, pharmaceutically acceptable salts or stereoisomers thereof and a pharmaceutically acceptable carrier therefor.

8. The pharmaceutical composition of claim 7 wherein said compound is a calcium sensing receptor antagonist.

* * * * *